United States Patent [19]
Eisenbach

[11] Patent Number: 5,849,713
[45] Date of Patent: Dec. 15, 1998

[54] CHEMOTACTIC FACTORS FOR HUMAN SPERMATOZOA AND THEIR USE IN HUMAN ASSISTED FERTILIZATION

[75] Inventor: Michael Eisenbach, Rehovot, Israel

[73] Assignee: Yeda Research and Development Co. Ltd., Rehovot, Israel

[21] Appl. No.: 464,894

[22] PCT Filed: Jan. 12, 1994

[86] PCT No.: PCT/US94/00677
§ 371 Date: Jan. 5, 1996
§ 102(e) Date: Jan. 5, 1996

[87] PCT Pub. No.: WO94/15630
PCT Pub. Date: Jul. 21, 1994

[30] Foreign Application Priority Data

Jan. 13, 1993 [IL] Israel ......................................... 104383

[51] Int. Cl.⁶ .............................. A61K 38/02; C07K 1/20; C07K 14/47; G01N 33/48

[52] U.S. Cl. ............................... 514/21; 435/806; 436/63; 436/906; 530/300; 530/344; 530/350; 530/417; 530/419; 530/850

[58] Field of Search .......................... 514/21, 8; 530/350, 530/416, 417, 300, 322, 395, 419, 850, 853, 344; 435/806; 436/906, 63

[56] References Cited

U.S. PATENT DOCUMENTS 4,767,703  8/1988  Ax et al. ..................................... 435/29
4,772,554  9/1988  Ax et al. ..................................... 435/23

OTHER PUBLICATIONS

Manor et al, Purification of Chemotactic Factors . . . Molecular Biology of the Cell, Oct. 1993, vol. 4, p. 139a, Abstr. 809.

Ralt et al. Sperm Attraction to a Follicular Factors(s) Proc. Natl. Acad. Sci. Apr. 1991, vol. 88, pp. 2840–2844.

Lee, Shuang–Lin, Yu–Min Kuo, Chin–Cheng Kao, Chuang–Ye Hong, and Yau–Huei Wei; "Purification of a Sperm Motility Stimulator from Porcine Follicular Fluid"; Comparitive Biochemistry and Physiology; vol. 101B, No. 4; pp. 591–594; 1992.

Lachapelle. MH, R. Bouzayen, J. Langlais, K. Jarvi, J. Bourque, and P. Miron; "Effect of Lysoplatele–Activating Factor on Human Sperm Fertilizing Ability"; Fertil Steril; vol. 59, No. 4; Abstract; Apr. 1993.

Giorgetti C., E. Hans, J.L. Spach, P. Auquier, and R. Roulier; "In–Vitro Fertilization in Cases with Severe Sperm Defect Use of a Swim–Across Technique and Medium Supplemented with Follicular Fluid"; Human Reproduction; vol. 7, No. 8; Abstract; 1992.

*Primary Examiner*—Jeffrey E. Russel
*Attorney, Agent, or Firm*—Browdy and Neimark

[57] ABSTRACT

The invention relates to chemotactic factors for human spermatozoa that are purifiable from human follicular fluid. The factors are of peptidic and hydrophilic nature and have, one, a molecular size of about 13 kDa and, the other, an apparent molecular size smaller than 1.3 kDa, as determined by high pressure gel filtration. They are for use in procedures related to human fertilization, such as in various types of assisted fertilization, particularly artificial insemination, in vitro fertilization, micromanipulation and direct microinjection of sperm into oocytes.

21 Claims, 19 Drawing Sheets

F I G. 10B
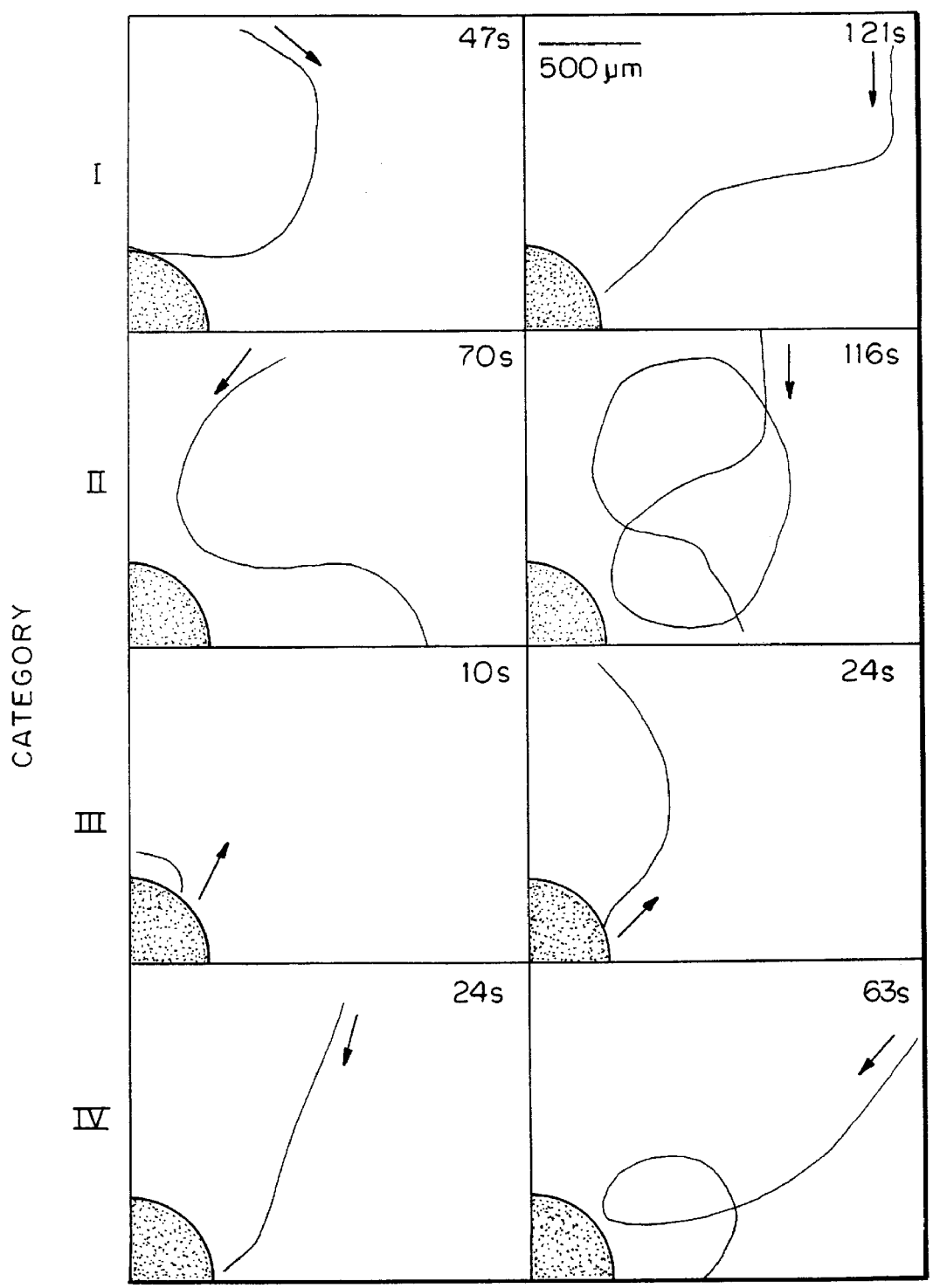

FIG. 23

| Procedure | Material | Relative activity (dilution) |
|---|---|---|
| Precipitation in 90% Acetone | Human Follicular Fluid → Precipitate | None |
| | Supernatant | $1.8\,(10^5)$ |
| Size Exclusion HPLC Column | The Rest | None |
| | 13 kDa | $1.9\,(10^5)$ |
| | <1.3 kDa | $1.6\,(10^5)$ |
| Reversed Phase HPLC Column | The Rest | None |
| | 20% Acetonitrile | $1.8\,(10^5)$ |
| | The Rest | None |
| | 0% Acetonitrile | $1.9\,(10^6)$ |
| Ion Exchange Column | The Rest | None |
| | Void Volume | $1.8\,(10^5)$ |

CHEMOTACTIC FACTORS FOR HUMAN SPERMATOZOA AND THEIR USE IN HUMAN ASSISTED FERTILIZATION

FIELD AND BACKGROUND OF THE INVENTION

The present invention relates generally to the field of human fertilization, and more particularly to human factors purifiable from human follicular fluid exerting both chemotactic and chemokinetic activities on human spermatozoa. The invention further concerns various treatment and diagnostic procedures related to human fertilization.

The problem of infertility afflicts about 10% of all couples. Of these, about 40–50% are related to female disorders and about 40% to male disorders, the remaining 10–20% of the cases lacking explanation. There is an ever growing number of procedures for the diagnosis and treatment of female sterility, while means for the treatment of male infertility or of infertility caused by defects in the sperm-egg interactions are quite limited.

One of the questions in mammalian fertilization, in general, and in human fertilization, in particular, was whether the egg communicates with spermatozoa in the female genital tract before the actual contact between them, or whether the sperm-egg contact is coincidental. A common mode of communication in nature is chemotaxis (i.e., the response of motile cells or organisms to the gradient of a chemical stimulus, resulting in modulation of the direction of travel so as to approach an attractant or to move away from a repellent), often accompanied by chemokinesis (i.e., a change in swimming speed in response to a chemical stimulus). Sperm chemotaxis is known to occur in species with external fertilization, primarily in metazoa whose females spawn their eggs into sea water before fertilization. Animal sperm attractants are peptides or proteins with molecular sizes varying from 1.5 kDa for sea urchin sperm attractant to 25 kDa for the sperm attractant of the siphonophore *Muggiaea atlantica*. Sperm chemotaxis is less obvious in species with internal fertilization, where very large numbers of spermatozoa (ca. $10^7$–$10^9$ in mammals) are ejaculated directly into the female reproductive tract; there, a sufficient number may reach the egg coincidentally, and a need for a directed movement or for sperm chemotaxis is not self-evident. However, recent studies indicate that sperm chemotaxis is also present in mammals.

Follicular fluids have a large number of substances, such as steroids, lipids, lipid proteins, peptide hormones, growth factors, etc., that affect sperm functions such as motility and metabolism.

In a previous study (Ralt et al., 1991), the inventors have shown that human spermatozoa accumulated in follicular fluid in vitro and that sperm attraction to follicular fluid correlated with egg fertilizability. It was thus suggested that the follicular fluid may contain a factor(s) released by the egg or its surrounding cells that is capable of attracting sperm. However, no factor has been isolated and characterized in this previous study, nor was the nature of the attraction identified.

SUMMARY OF THE INVENTION

It has now been found, in accordance with the present invention, that by precipitation of human follicular fluid with a protein-precipitating organic solvent, e.g. 90% acetone, the sperm chemotactic activity is found in the supernatant and not in the precipitate. Further fractionation of the acetone supernatant by size-exclusion chromatography followed by reversed-phase chromatography lead to two active fractions of peptidic nature exhibiting sperm chemotaxis—one containing a chemotactic factor with molecular size of about 13 kDa and the other a chemotactic factor with apparent molecular size smaller than 1.3 kDa (<1.3 kDa factor, herein).

The molecular size of the chemotactic factors was determined by high pressure gel filtration using a Bio-Sil TSK-125 600×7.5 mm column (Bio Rad, CA) and elution with 100 mM phosphate-buffered saline (PBS) (pH 7.4) at room temperature. Two fractions exhibiting sperm chemotactic activity were obtained: a first active fraction eluted at 17.0–17.5 min corresponding to molecular size of 13±1 kDa and a second fraction eluted at 25.0–25.5 min after the 1.3 kDa marker and after sodium azide, thus corresponding to an apparent molecular size smaller than 1.3 kDa. The two factors will be referred to in the specification as the 13 kDa factor and the <1.3 kDa factor, it being understood that these are molecular sizes established as described above.

It was further found that the two active fractions can also be obtained by applying human follicular fluid to size-exclusion chromatography directly.

The sperm chemotactic factors of the invention cause not only chemotaxis but also chemokinesis and hyperactivation-like motility of human spermatozoa, the chemotactic activity being concentration dependent.

Further characterization of the chemotactic factors has shown that they are of hydrophilic nature, because after precipitation of the 90% acetone supernatant of human follicular fluid with 100% acetone, the chemotactic activity was found predominantly in the pellets. In addition, they were found to be pronase sensitive, thus indicating that they are, at least in part, of peptidic nature.

The invention thus relates to purified chemotactic factors for human spermatozoa purifiable from human follicular fluid, said factors being pronase sensitive and of hydrophilic nature, characterized by:

(i) they are selected from a group consisting of a factor having a molecular size of about 13 kDa and a factor having a molecular size smaller than 1.3 kDa, the molecular sizes being determined by high pressure gel filtration using a Bio-Sil TSK-125 600×7.5 mm column and elution with 100 mM PBS (pH 7.4) at room temperature;

(ii) they cause human sperm chemotaxis and chemokinesis and, ultimately, hyperactivation-like motility;

(iii) their sperm chemotactic activity is concentration dependent;

(iv) when purified from human follicular fluid or from the 90% acetone supernatant thereof by high pressure gel filtration as in (i) above, the 13 kDa chemotactic factor is eluted at 17.0–17.5 min and the <1.3 kDa chemotactic factor is eluted at 25.0–25.5 min, the specific sperm chemotactic activity (per protein content) of each factor being at least 1,000 fold higher than that of the original follicular fluid; and (v) when purified by reversed-phase HPLC C18 column from the supernatant of human follicular fluid precipitated with 90% acetone or from the active fractions eluted from the column described in (i) above, the sperm chemotactic activity of the 13 kDa factor is eluted at 20% acetonitrile, and the sperm chemotactic activity of the <1.3 kDa factor is eluted at 0% acetonitrile, the specific chemotactic activity (per protein content) of each factor being at least 10,000 fold higher than that of the original follicular fluid.

The purified factors, after elution from the reversed-phase column, show a specific chemotactic activity (per protein content) at least 10,000 fold higher than that of the original follicular fluid, such as 18,000 fold higher (for the <1.3 kDa factor) or 53,000 fold higher (for the 13 kDa factor).

The invention further relates to pharmaceutical compositions comprising a sperm chemotactic factor according to the invention for use in several diagnostic and treatment procedures related to human fertilization, such as in methods for determining the fitness of human sperm for fertilization or for predicting the fitness of a human ovum for fertilizability, and in processes of fertilizing a human ovum, such as various types of assisted fertilization, and particularly in artificial insemination, in in vitro fertilization (IVF), in micromanipulation and in direct microinjection of sperm to oocytes.

Each point represents 6 determinations±SEM. The results with the two populations were similar, as revealed from Student's t-test (P=0.51). Empty columns, BWW-containing capillaries; hatched columns, follicular fluid-containing capillaries.

Figure 6:
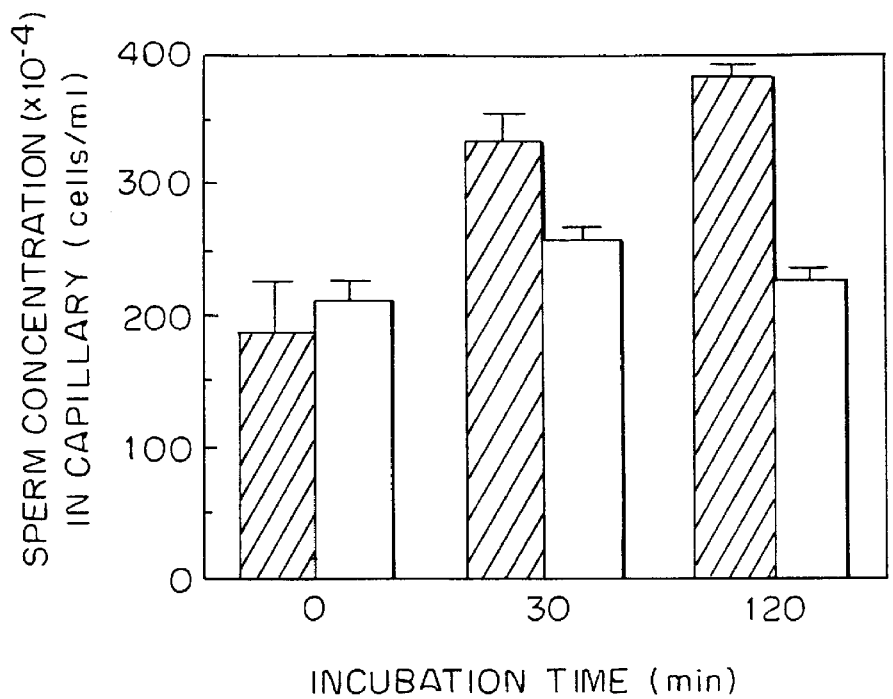

FIG. 6 shows the effect of sperm preincubation on sperm accumulation. The experiment was carried out as in FIG. 3, except that the spermatozoa were incubated prior to the experiment at 37° C. under 5% $CO_2$ for the indicated periods of time and the duration of each assay was 40 min. (This is distinct from FIG. 3, where the length of the preincubation was constant and the duration of the assay varied.) The number of spermatozoa in each capillary was estimated by the endopeptidase assay. The figure contains the results of a typical experiment (out of 9 experiments in total). Empty columns—BWW-containing capillaries; hatched columns—follicular fluid-containing capillaries.

Figure 7:
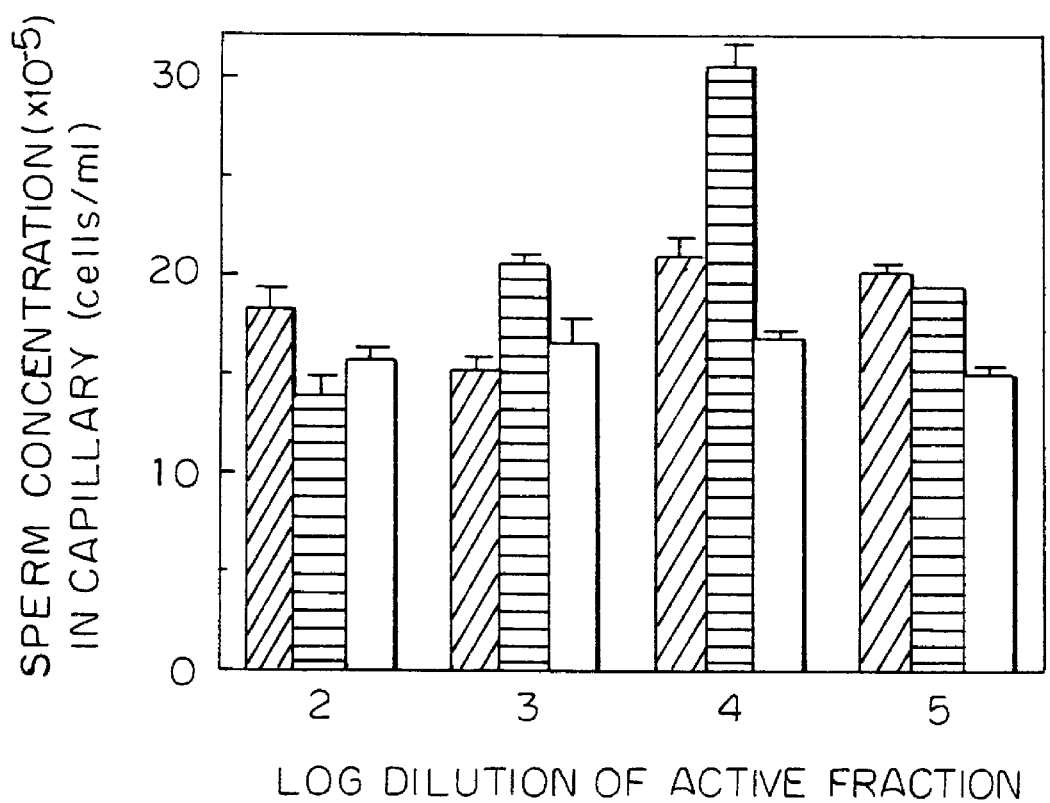
Figure 8A:
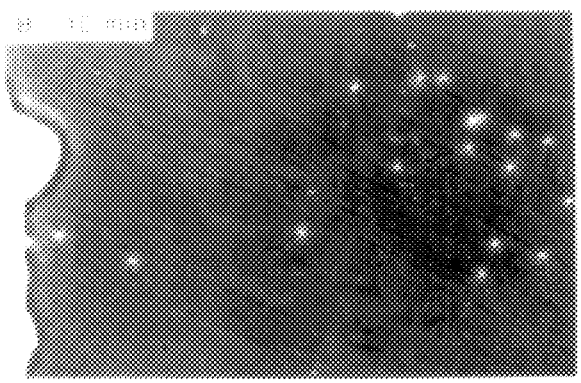
Figure 8B:
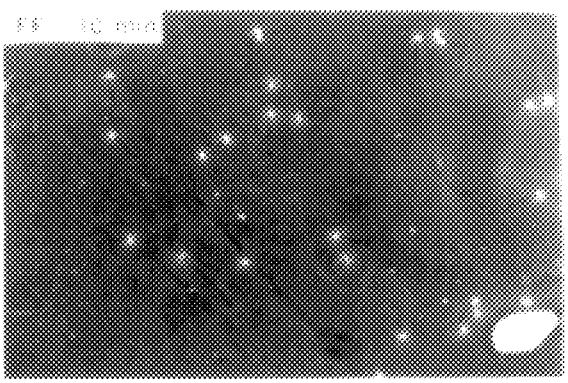
Figure 8C:
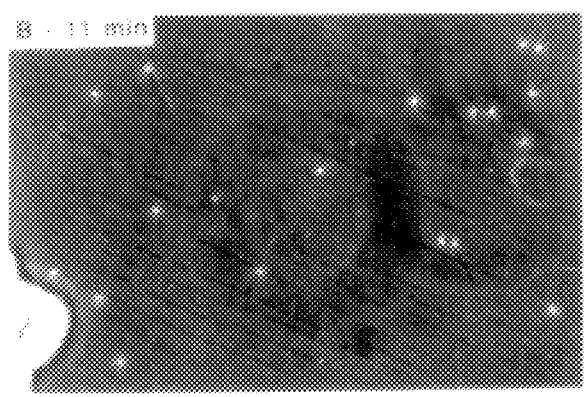
Figure 8D:
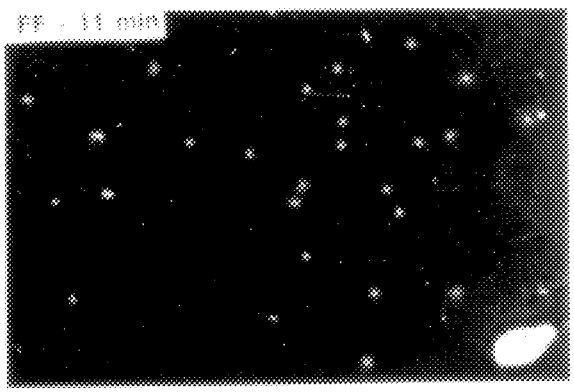
Figure 8E:
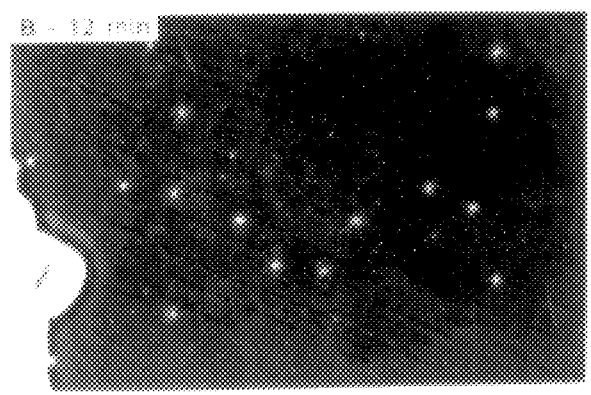
Figure 8F:
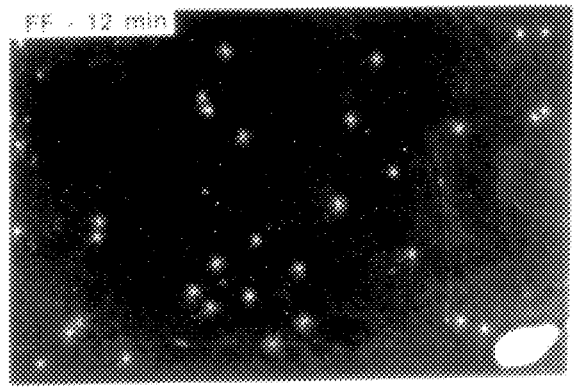

FIG. 7 shows concentration dependence of sperm accumulation in capillary assays with a descending gradient of follicular fluid or no gradient at all. Capillary assays were carried out as in Table 1, except that they were performed at room temperature (25° C.) and that the active fraction of follicular fluid, prepared by 90% acetone precipitation, was used instead of the whole fluid. The figure contains the results of a typical experiment (out of 13 experiments in total). Each point represents the mean of 6 determinations±SEM. The active fraction was diluted in BWW to the extent indicated in the figure. Gray columns, active fraction in the well (like setting no. 1 in Table 1); black columns, active fraction in both the well and capillary (like setting no. 2); empty columns, BWW in both the well and capillary (like setting no. 3).

FIGS. 8A–8F show shows distribution of spermatozoa near wells containing follicular fluid and BWW in a microscopic assay for chemotaxis. The experiment was carried out as described in Materials and Methods. The spermatozoa are observed in the photographs as small dots. The photographs were taken near the BWW-containing (B) and follicular fluid-containing (FF) wells at 1 min intervals, starting at 10 min after the chamber had been sealed (the time at which each of the photographs was taken is shown at the upper left corner). The follicular fluid was 1:10 diluted in BWW. The rim of the B well is observed at the left side of each of the left-side photographs; the FF well was at the right side of each of the right-side photographs (not seen in the photographs).

Figure 9A:
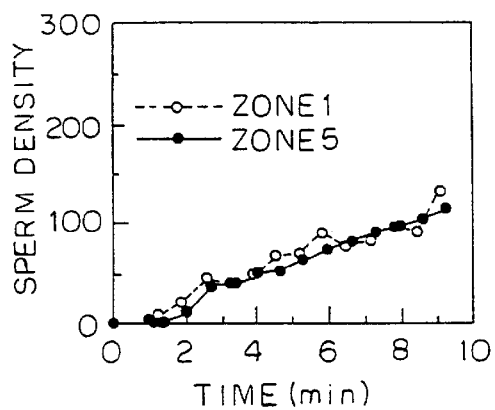
Figure 9B:
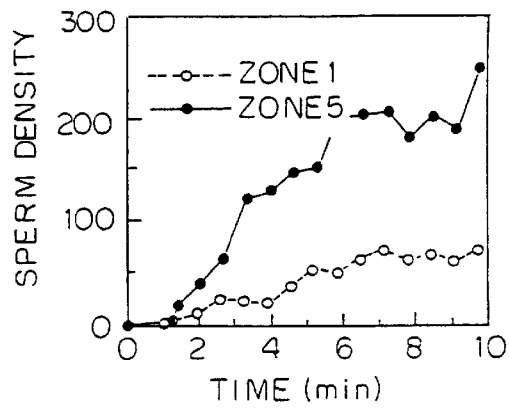
Figure 9A:
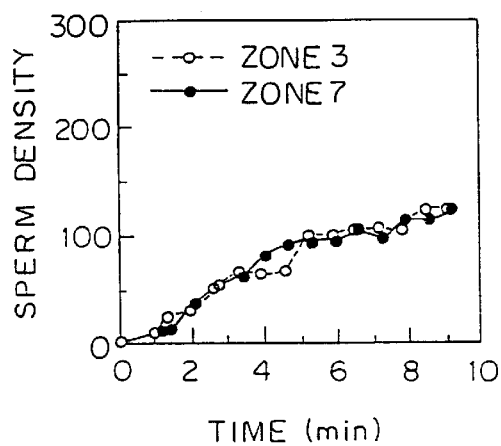
Figure 9B:
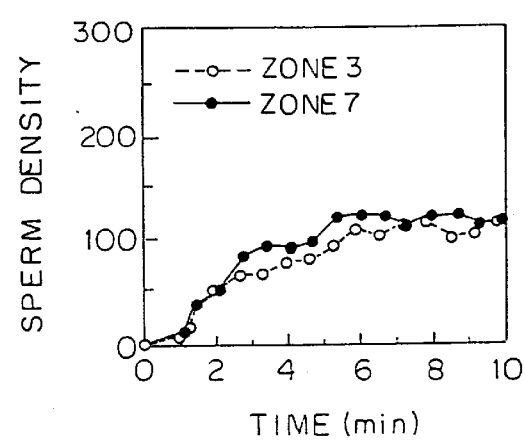
Figure 9B:
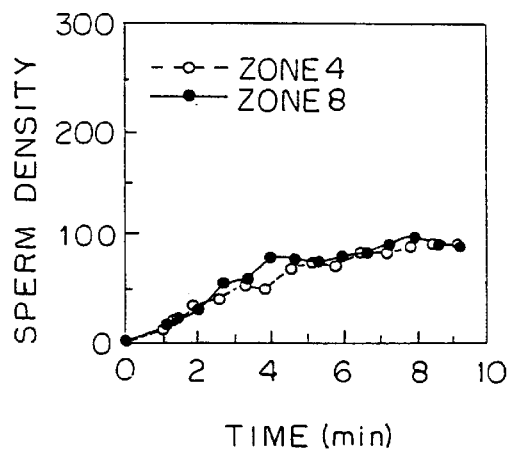
Figure 9B:
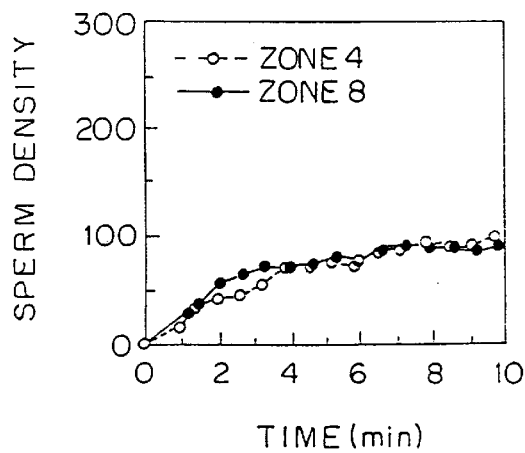

FIGS. 9A–B show time-dependent distribution of spermatozoa in a microscopic assay for chemotaxis. The sperm density is expressed in spermatozoa per $mm^2$. The sperm concentration in the well was $5 \times 10^8$ cells/ml (empty circles), zones 1–4; (filled circles), zones 5–8. Panels A, both wells containing BWW; Panels B, left well (near zones 1–4) containing BWW, right well (near zones 5–8) containing the active fraction (10-fold diluted) prepared by 90% acetone precipitation. The figure represents a typical experiment (out of 6 in total) in which both parts A and B were carried out with the same sperm sample. Additional experiments were carried out with different sperm samples (from 10 donors) which included part A only (14 experiments) or part B only (129 experiments).

Figure 10A:
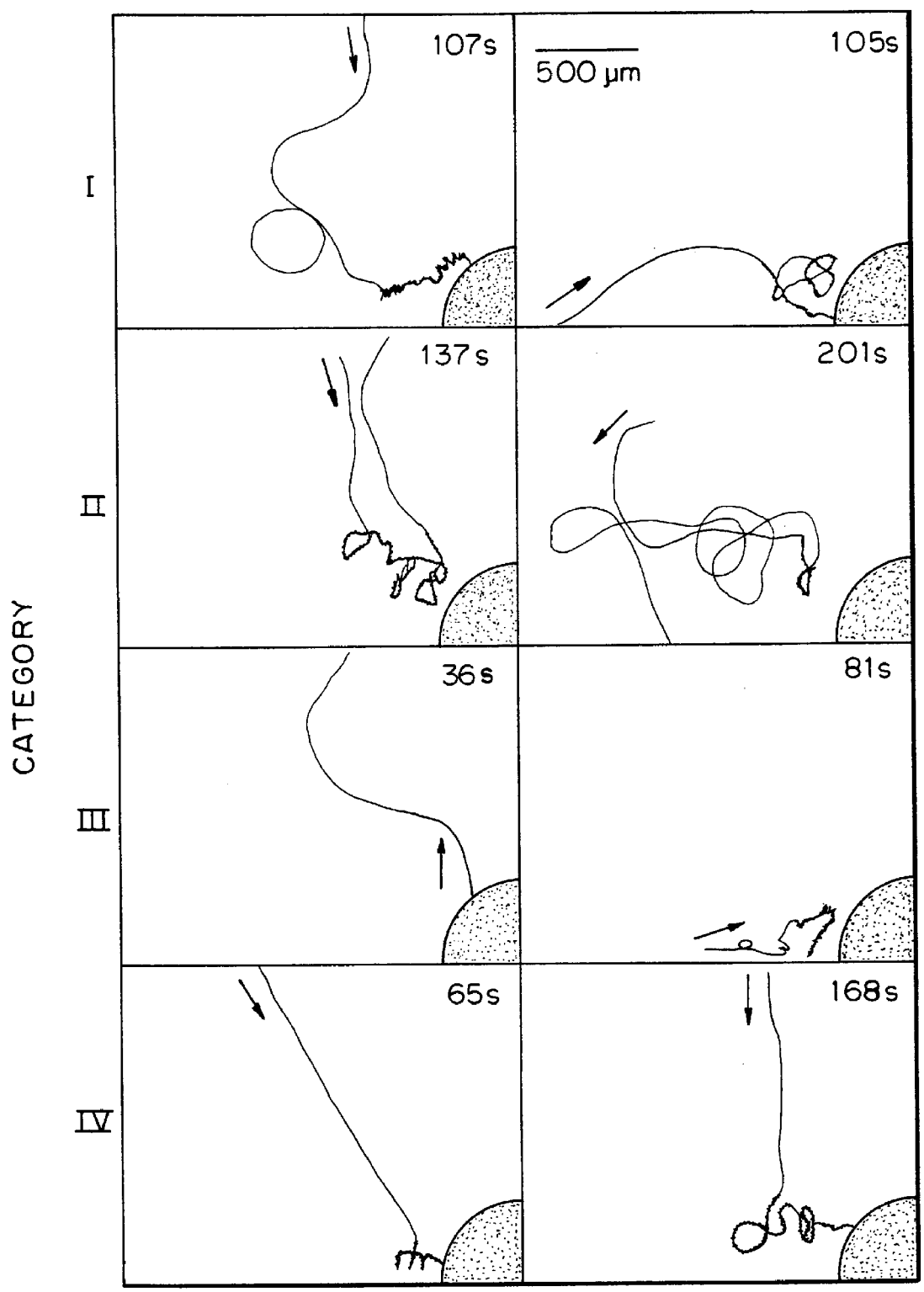
Figure 10C:
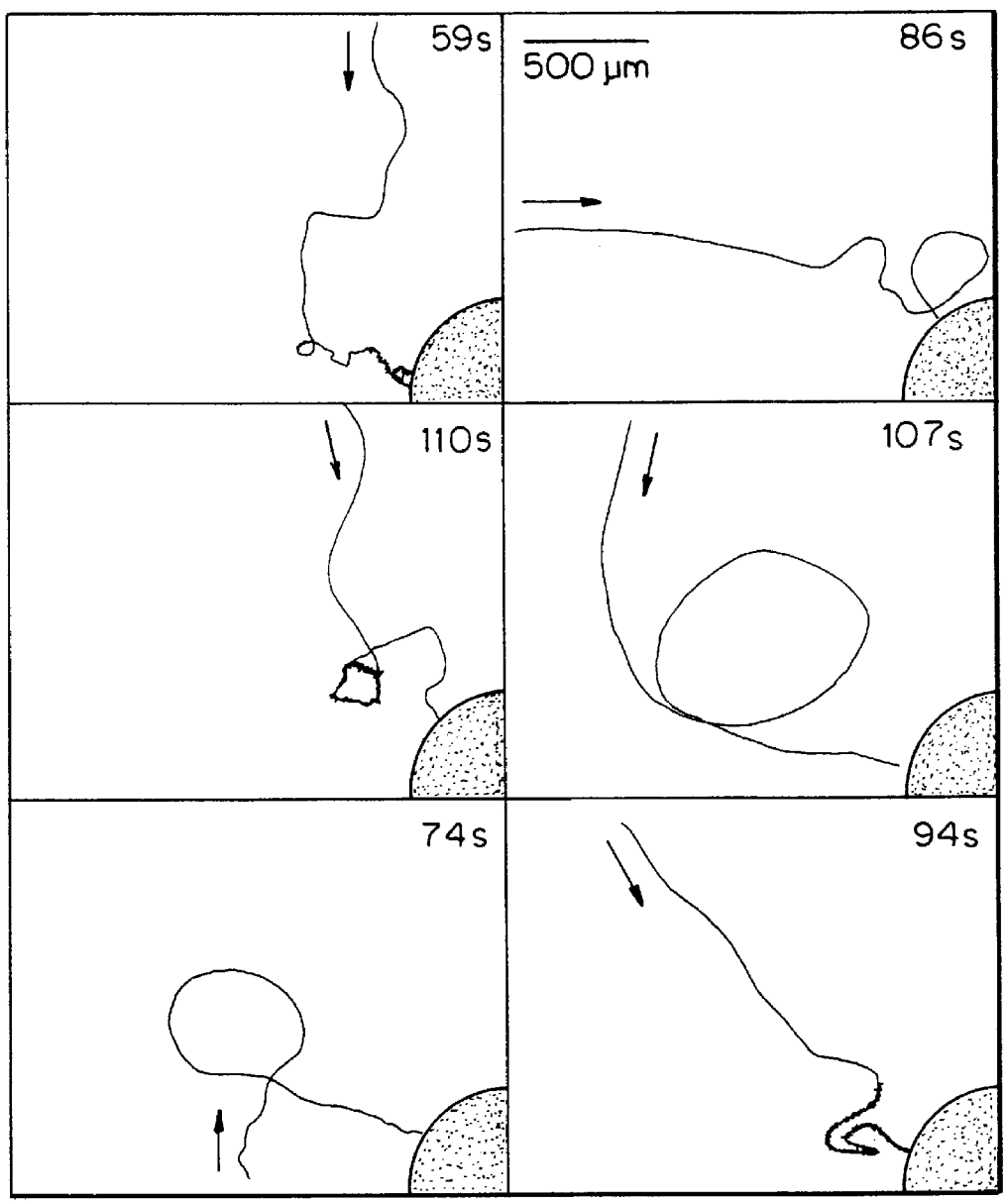

FIGS. 10A–C show representative trajectories of spermatozoa in the sealed chamber. The control well (left) contained BWW and the test well (right) contained the active fraction (10-fold diluted) prepared by 90% acetone precipitation. The motion of the spermatozoa was monitored and the recorded field was 2.0×2.5 mm. The duration of each track is indicated at the top right corner of each panel. The arrows indicate the direction of progression of each trajectory. Panels A, sperm trajectories near the active fraction-containing well; Panels B. sperm trajectories near the BWW-containing well; Panels C, representative additional trajectories of category 1 near the active fraction-containing well. The categories are those listed in Table 3.

Figure 11:
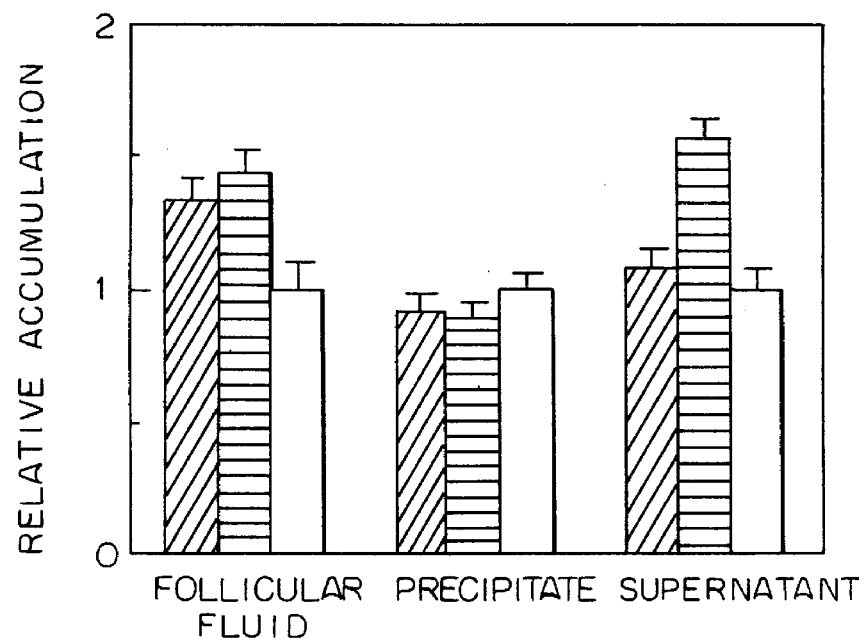

FIG. 11 depicts chemotactic and chemokinetic activities per volume of follicular fluid before and after precipitation by 90% acetone. The chemotactic and chemokinetic activities of the supernatant and pellet fractions were determined ($10^3$-fold diluted) by assays carried out as in Table 1. The protein concentrations of the original fluid, precipitate, and supernatant in the assay (after dilution) were 15, 8.5 and 0.24 $\mu$g/ml, respectively. Each column in the figure represents 36 determinations (3 donors of spermatozoa; 2 experiments with each donor; 6 capillaries in each experiment), normalized according to the accumulation of spermatozoa in BWW±SEM. Gray columns, test solution in the well (like setting no. 1 in Table 1); black column, test solution in both the well and capillary (like setting no. 2); empty columns, BWW in both the well and capillary (like setting no. 3).

Figure 12:
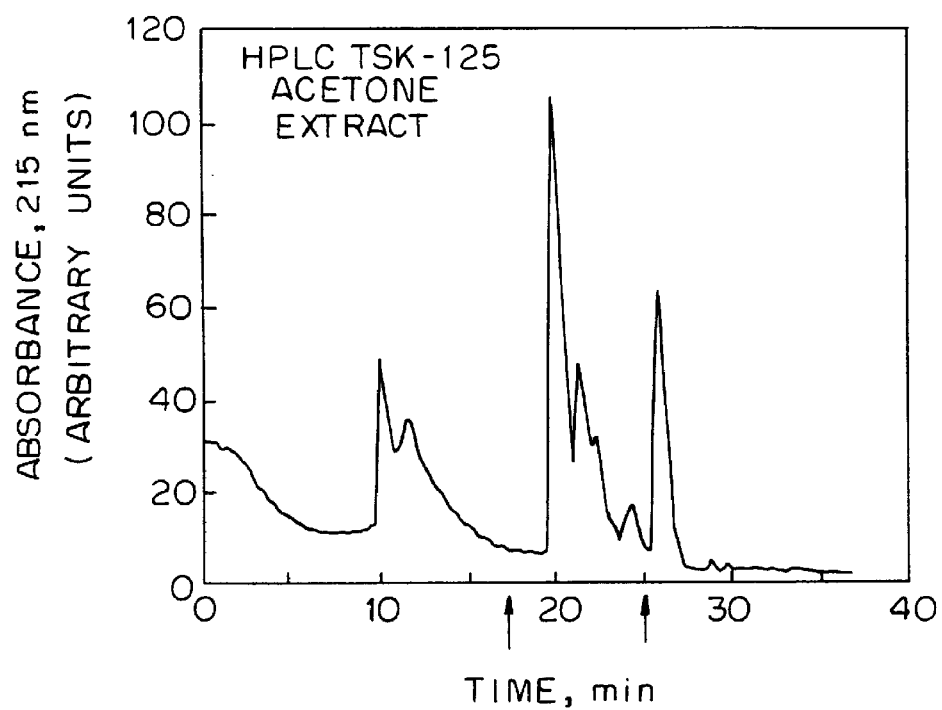

FIG. 12 shows elution profile of acetone supernatant from a size-exclusion HPLC column (TSK 125). The left arrow points at the fraction of 13 kDa (eluted at 17.0–17.5 min) and the right arrow at the fraction of the <1.3 kDa (eluted at 25.0–25.5 min). The absorbance was at 215 nm.

Figure 13A:
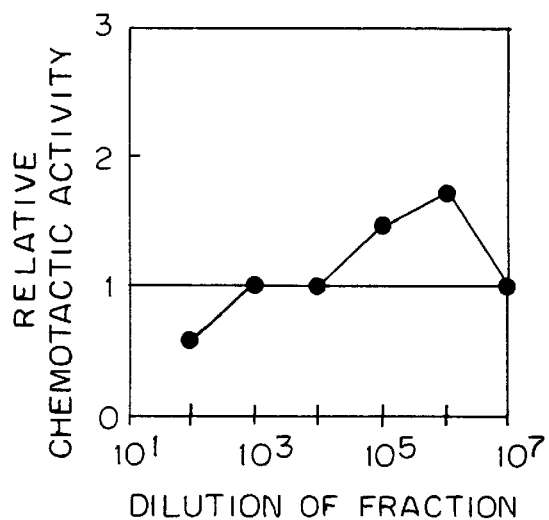
Figure 13B:
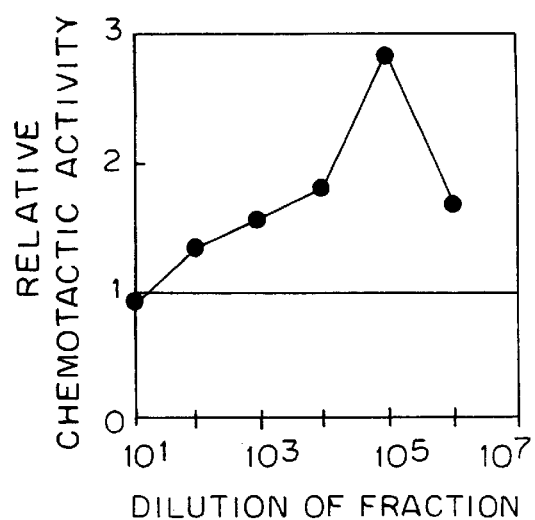

FIGS. 13A–B illustrate concentration dependence of chemotactic activity of the <1.3 kDa (A) and the 13 kDa (B) fractions eluted from the size-exclusion column. The experiment was carried out by the microscopic assay. The relative chemotactic activity was calculated as the ratio between the integrated area beneath the curve (like in FIG. 9) representing zone 5 and that beneath the curve representing zone 1. A relative chemotactic activity of value 1 means, herein in the specification, no activity.

Figure 14:
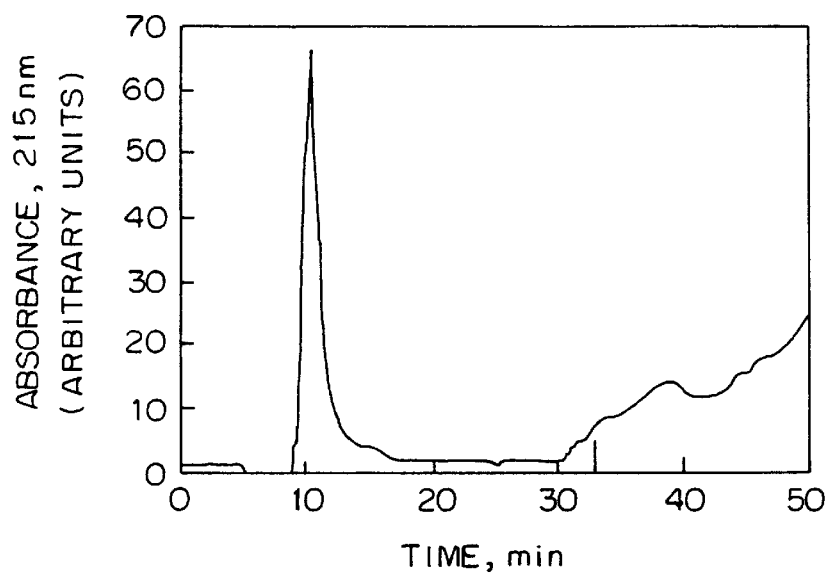

FIG. 14 depicts elution diagram of the 13 kDa chemotactic factor from a reversed-phase HPLC column C18. The arrow points at fractions #33–34 (eluted at 34.0 min). The absorbance was at 215 nm.

Figure 15:
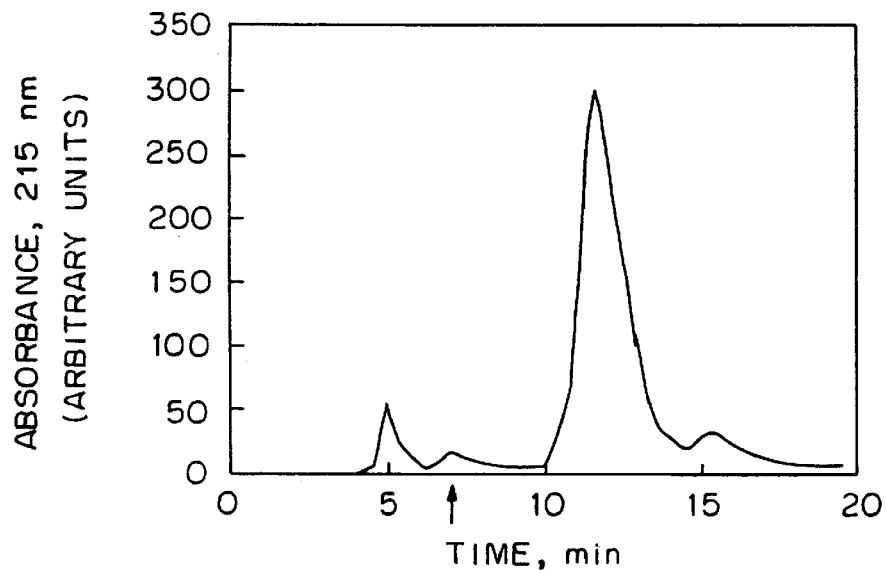

FIG. 15 depicts elution diagram of the <1.3 kDa chemotactic factor from a reversed-phase HPLC column C18. The arrow points at fractions #6–8 (eluted at 7.0–8.0 min). The absorbance was at 215 nm.

Figure 16A:
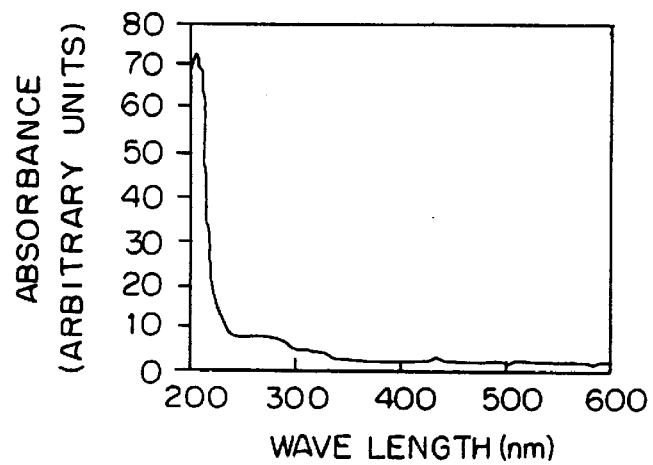
Figure 16B:
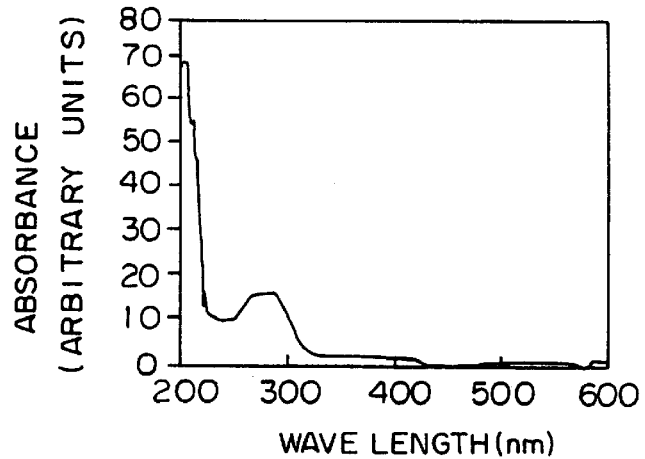

FIGS. 16A–B depict the absorbance spectrum of the 13 kDa(B) and the <1.3 kDa(A) chemotactic factors.

Figure 17:
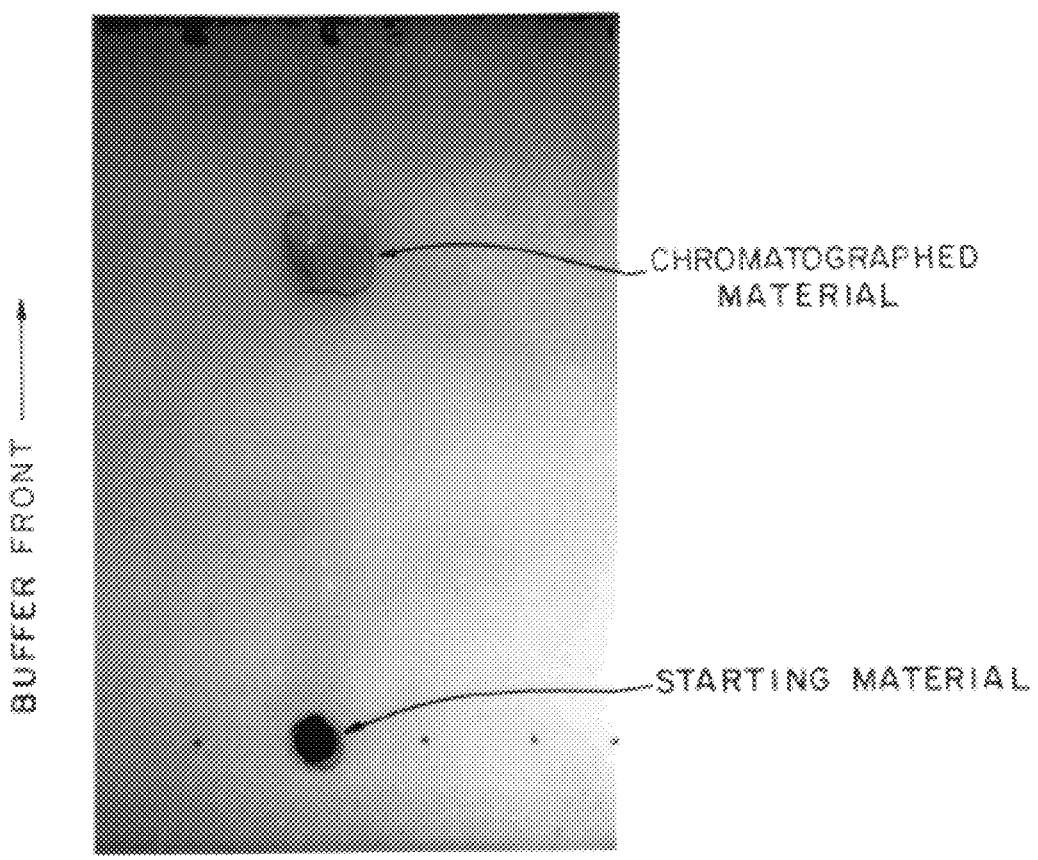

FIG. 17 depicts thin layer chromatography of the <1.3 kDa chemotactic factor derived from the reversed-phase HPLC column. The spots were visualized with a short wavelength UV lamp.

Figure 18A:
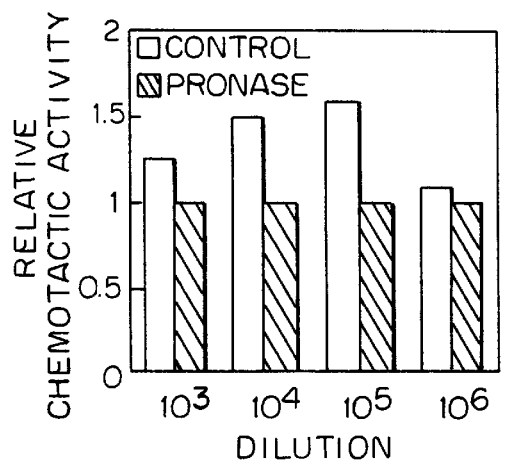
Figure 18B:
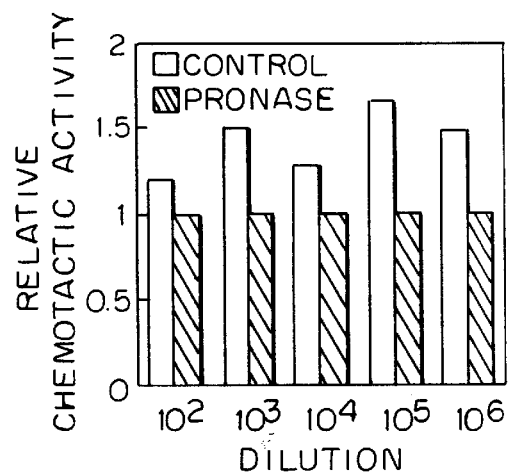

FIGS. 18A–B show concentration dependence of chemotactic activity of the <1.3 kDa and the 13 kDa factors before and after pronase-E treatment. The activity was determined by the microscopic assay as described in Materials and Methods. The relative chemotactic activity was calculated as in FIG. 13. Black columns, relative activity of the fractions without pronase-E treatment. Gray columns, relative activity after incubation with pronase-E. Panel A. Relative chemotactic activity of the <1.3 kDa factor. Panel B. Relative chemotactic activity of the 13 kDa factor. The figure represents a typical experiment out of 4.

Figure 19:
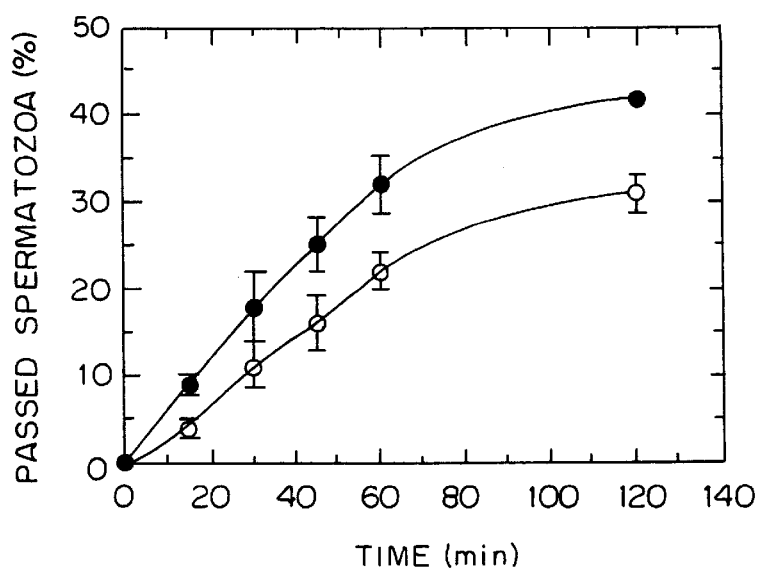

FIG. 19 illustrates sperm separation as a function of time. The separation was carried out as described in Materials and Methods, for the duration shown in the figure, with chamber no. 2 containing either diluted attractant (filled circles) or, as a control, BWW (empty circles). The sperm concentration used for the separation was $4\times10^7$ cells/ml. After incubation at room temperature for the indicated periods of time, the sperm suspensions from both chambers were collected, washed and counted. The figure (mean±S.D. of 3 experiments) presents the percentage of spermatozoa which passed to chamber no. 2 during the various separation periods.

Figure 20:
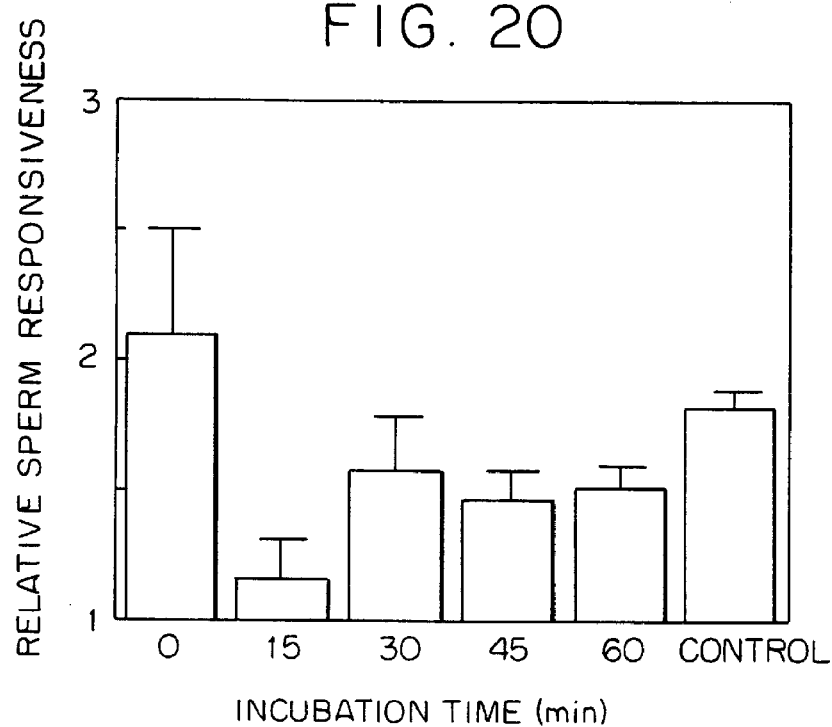

FIG. 20 shows relative responsiveness of spermatozoa after various incubation periods in diluted attractant. The dilution of the attractant was identical to the dilution used for the sperm separation on the day of the experiment ($10^3$–$10^4$ fold dilution). Following incubation of the original sperm population for the designated periods of time, the spermatozoa were washed by 2 cycles of centrifugation (120.g, 15 min) with BWW and then assayed. The relative responsiveness was calculated as in Table 6. The control column stands for the responsiveness of the original spermatozoa incubated in BWW in the absence of the attractant for the duration of the experiment. The results represent the mean±SEM of 4 experiments carried out with a single sperm donor and with active fractions of 3 follicular fluids (all used also in Table 6). The activity at t=0 was significantly different (95% significance) from the activities at 15, 45 and 60 min (calculated by ANOVA with repeated measures followed by Fisher's LSD multiple comparison test).

Figure 21:
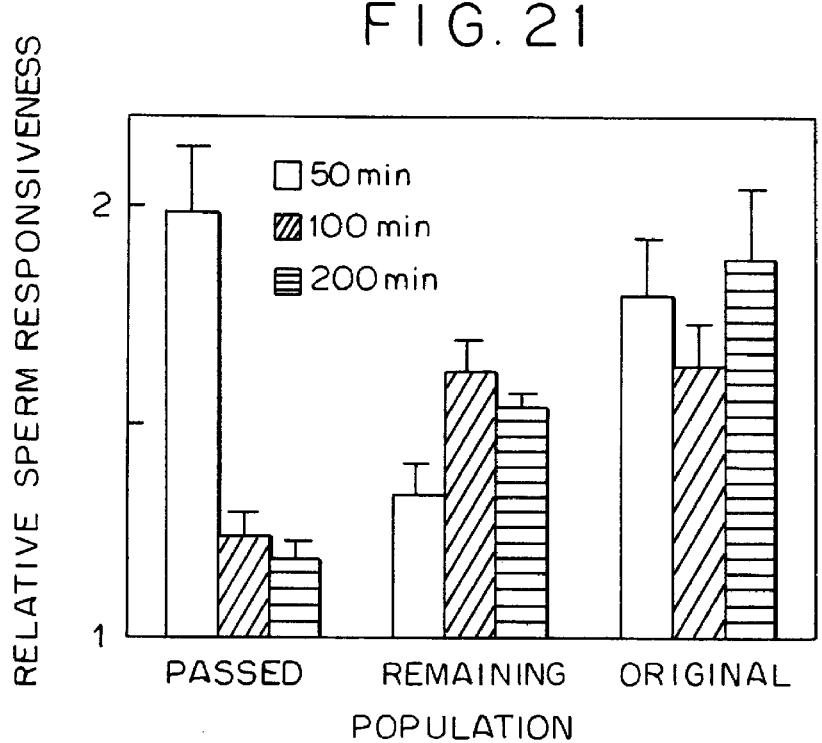

FIG. 21 shows that the responsiveness of each sperm subpopulation changes with time. The relative responsiveness was calculated as in Table 6. The time points represent the periods of time since the removal of the attractant (t=0 considered as 10 min after initiation of the first centrifugation during the washing procedure that followed the separation into subpopulations). The earliest time at which the responsiveness could be assayed was 50 min after the separation. The original sperm population was analyzed at the same time points. The results represent the mean±SEM of 7 experiments carried out with 3 sperm donors and active fractions of 4 different follicular fluids. The significance of the difference between the passed subpopulation at 50 min and the other populations at all times, as well as the difference between the remaining subpopulations at 50 min and at 100 min was 95%.

Figure 22:
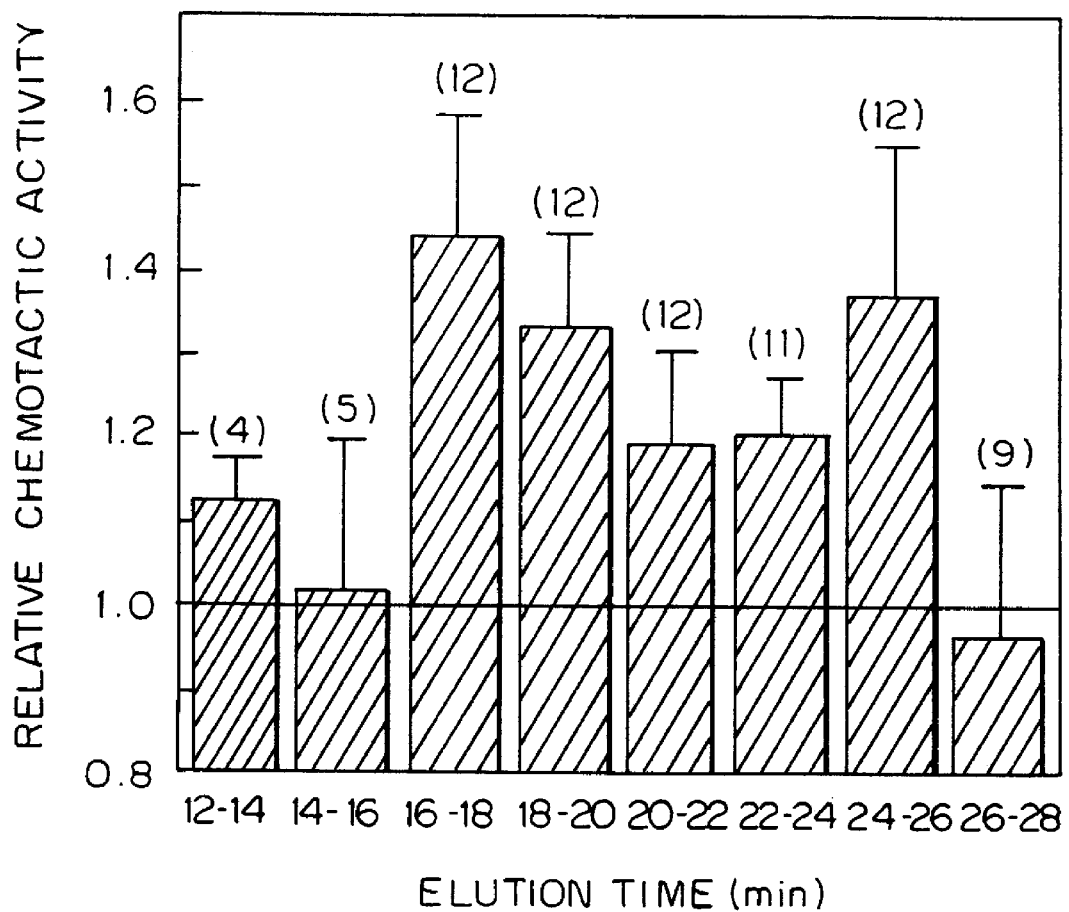

FIG. 22 shows the relative chemotactic activity of fractions of follicular fluid eluted from a size-exclusion column.

FIG. 23 shows a flow chart of the fractionation procedure.

DETAILED DESCRIPTION OF THE INVENTION

Human spermatozoa are accumulated in vitro in diluted follicular fluids obtained from follicles of which the eggs have been fertilized, but the extent of the net accumulation is low (Ralt, et al., 1991). By using capillary assays with a variety of settings (ascending or descending gradient of follicular fluid, or no gradient at all), and microscopic assays in which individual spermatozoa could be followed, it was found according to the present invention that the accumulation in follicular fluid is the result of both sperm chemotaxis and chemokinesis. The cause of the low net accumulation was found to be physiological rather than technical, and to reflect the chemotactic responsiveness of only a small fraction of the sperm population. This low net accumulation made any chemotaxis assay very vulnerable to deviations.

According to the invention, the optimal conditions, which involved sperm preincubation (possibly to induce sperm capacitation) and proper dilution of follicular fluid, were determined, thus enabling study of human sperm chemotaxis and allowing identification of the chemotactic factors. We identified the chemotactic factors (by fractionation of the follicular fluid) as molecules of peptidic nature of molecular sizes of about 13 kDa and <1.3 kDa. This is the first time that sperm chemotaxis to follicular factor(s) in mammals is established and that a distinction is made between true chemotaxis and other processes which might cause sperm accumulation.

The chemotactic activity of the chemotactic factors of the invention is assayed by the microscopic assay and/or the capillary assay described hereinafter in Materials and Methods and Examples.

In one embodiment, high MW proteins in the follicular fluid were precipitated with 90% acetone, and the chemotactic activity of the acetone supernatant was found to be substantially higher than that of the original follicular fluid, even though the protein content in the supernatant was over 60 fold lower than in the follicular fluid. Then, by using a size-exclusion HPLC column, two fractions of follicular fluid with positive chemotactic activity were found : one having a molecular size smaller than 1.3 kDa, and the other about 13 kDa, indicating that the follicular fluid contains two chemotactic factors (the possibility that there is only one factor with several isoforms or polymeric forms should also be considered). The factors were further purified by reversed-phase chromatography on an HPLC C-18 column. The <1.3 kDa factor was further purified by cation exchange (Dionex) chromatography. Both factors were found to be pH stable and protease sensitive. As described above, most of the chemotactic factors or attractants for spermatozoa that have been identified in animals with external fertilization are peptides or proteins of various sizes (1–25 kDa), heat stable and sensitive to proteases. The human chemotactic factors of the present invention are not identical to any of the known factors.

It was further found according to the invention that, depending on the original motility of the spermatozoa, the chemotaxis process is often accompanied by chemokinesis. Assuming that the role of human sperm chemotaxis in vivo is selection of those spermatozoa that have the ability to fertilize the egg at the time of ovulation or after it (Eisenbach, et al., 1992), the physiological role of sperm chemokinesis would possibly be to enhance the movement of the selected spermatozoa and thus to improve their competitiveness with respect to the non-selected ones. We also found that when spermatozoa approach the chemotactic factor(s) by chemotaxis they eventually acquire a hyperactivation-like motility (a motility pattern associated with sperm capacitation and characterized by wide amplitude and marked lateral displacement of the head). A likely sequence of events may be that the spermatozoa sense a gradient of a chemotactic factor, follow the factor up the gradient while enhancing their speed of swimming, and, when they reach an optimal concentration of the factor (in vivo it is presumably a concentration that prevails near the egg), they become hyperactivated and consequently remain essentially in place in spite of their vigorous motility.

The present invention further comprehends procedures involving the human sperm chemotactic factor(s) of the present invention, such as determining the fitness of sperm for fertilization by determining the ability of a sperm sample to be attracted to the factor(s), and improving the in vitro fertilization process by adding the factor(s) to the incubating sperm and ovum, or a process for actually separating the fraction of sperm which is most attracted to the factor(s) for use in different procedures of assisted fertilization, including but not being limited to procedures of artificial insemination, such as intrauterine insemination, intraperitoneal insemination, intrafallopian insemination, in vitro fertilization (IVF), micromanipulation and direct microinjection to oocytes. For use in such processes the factor(s) of the present invention may be used alone or as active ingredients of pharmaceutical compositions together with a pharmaceutically acceptable carrier.

In a preferred embodiment, chromatographically-purified preparations of the chemotactic factor(s) are used, each of them alone or both together.

Among the utilities for the sperm-attracting compositions of the present invention is a process of assaying the fitness of a population of sperm for fertilization. The ability of the human sperm sample to be attracted to a human factor(s) capable of attracting sperm, in any of its various forms or purities, is directly related to the ability of that sperm sample to cause fertilization. In particular, the assay may be done on a number of sperm populations. The population with the greater ability to be attracted to the sperm-attracting composition is considered to be the population with the greatest fitness for fertilization. Indeed, our findings demonstrate that there is a correlation between the chemotactic responsiveness of the spermatozoa and capacitation.

A related utility for the chemotactic factor(s) of the invention is sperm improvement without physical separation of the cells. Preincubation of spermatozoa with the chemotactic factor(s) may be used for increasing the fraction of capacitated spermatozoa as pre-treatment for assisted in vivo and in vitro fertilization.

A related utility for the chemotactic factor(s) involves actually separating or selecting from a given sperm sample only those sperm cells which are most greatly attracted to the chemotactic factor(s). Any method of selecting the spermatozoa which are most responsive to the factor(s) may be used. For example, two wells connected by a tube can be provided, one well containing spermatozoa and the other containing the sperm-attracting preparation. A gradient of such factor would be formed along the tube and responsive spermatozoa would follow the gradient and accumulate in the other well. Another possibility is to make a gradient in a viscous medium by a gradient maker. Yet another possibility is to use a semi-solid medium in which spermatozoa are added at one end and a polymer soaked with the sperm-attracting composition is added at the other end. A gradient of the factor in this case will be made by sustained release from the polymer. Those of ordinary skill in the art will understand that many other chambers and vessels can be suggested, but that the principle would be the same in all cases. That portion of the sperm population that moves most rapidly in the direction of increasing concentration of factor is that which is most fit for fertilization processes.

Another aspect of the present invention is the prediction of the relative fitness of an ovum for fertilization. It has been found that ova from follicles having the greatest amount of the factor of the present invention in their follicular fluid are most likely to have positive fertilization. Thus, for example, the relative fitness of ova for in vitro fertilization can be determined by precipitating follicular fluid from the same follicle as the one in which the ovum was found, with a protein-precipitating organic solvent, diluting the dried supernatant with a buffer, and measuring the ability of that dried supernatant preparation to induce accumulation of sperm. The probability of fitness for fertilizability of a plurality of ova tested in this manner can be assigned based on the relative amount of factor capable of inducing sperm accumulation. Other approaches may also be used to assess the fertilizability of the egg, such as an immunochemical (ELISA, radioimmunoassay) using antibodies raised against the chemotactic factor(s). A greater probability of fitness for fertilizability is assigned to an ovum from a follicle that produces the fluid with a greater ability to attract sperm or with higher concentrations of the chemotactic factor(s). The assay may be carried out also in other body fluids, such as serum or urine, to which the chemotactic factors have been passed from the bursting follicle. Concentration of the factor(s) below a threshold concentration would indicate low probability of fertilization.

The factor(s) of the invention and compositions containing them may be also useful as contraceptive agents in intrauterine devices or in contraceptive foams and gels, since they mask the spermatozoa receptors and prevent them from reaching the egg. Another approach would be to use blockers of the sperm chemotaxis receptors.

The scope and content of the present invention will be further understood from a consideration of the following experiments and examples which are presented in a non-limiting manner.

EXAMPLES

In the examples the following materials and procedures will be used.

MATERIALS AND METHODS

Spermatozoa

Human ejaculates were collected by masturbation from normal healthy donors. Each ejaculate was allowed to liquefy at room temperature and then washed twice (using centrifugation at 120.g for 15 min) with Biggers, Whitten and Whittingham (BWW) medium (Biggers et al., 1971) [20 mM sodium lactate, 5 mM glucose, 0.25 mM sodium pyruvate, bovine serum albumin (fraction 96–99%) at 3 g/l, penicillin G at 0.08 g/l, streptomycin sulfate at 0.05 g/l, 95 mM NaCl, 4.8 mM KCl, 1.3 mM $CaCl_2$, 1.2 mM $KH_2PO_4$, and 1.2 mM $MgSO_4$ in 25 mM $NaHCO_3$ buffer pH 7.4] supplemented with HEPES (10 mM, pH 7.4) and 0.1% polyvinyl-pyrrolidone 40 (PVP, $M_r$ 40,000, Sigma) to reduce sperm adsorption. This solution is denoted herein in the specification as BWW. The spermatozoa were resuspended in BWW to a concentration of $1-2 \times 10^7$ cells/ml (for capillary assays) or $1-5 \times 10^8$ cells/ml (for microscopic assays) and, unless indicated otherwise, incubated for 2h at 37° C. under 5% $CO_2$.

Follicular fluid

Human follicular fluids were obtained from women undergoing transvaginal aspiration for in vitro fertilization, who had been pretreated with human menopausal gonadotropins for ovarian stimulation. Follicular fluids were filtered through a 0.45 μm Acrodisc filter to remove cells and cell debris. The filtrates were divided into 200 μl aliquots and stored at −20° C.

Acetone precipitation of follicular fluid

For 90% acetone precipitation, one portion of follicular fluid was mixed with 9 portions of cold acetone. The mixture was incubated on ice for 60 min and then centrifuged (640xg, 10 min). The resulting supernatant was dried in a SpeedVac concentrator (Savant Instruments, Farmington, N.Y.) and the pellet was dried under nitrogen. The dried supernatant and pellet were stored at −20° C. for no longer than one month. Prior to the experiments, they were diluted with BWW to the original volume of the follicular fluid.

For 100% acetone precipitation, a portion of the supernatant fraction from the 90% acetone precipitation was dried, and 100% acetone was added. The newly-formed pellet was separated from the supernatant by centrifugation and then dried and resuspended in 100% acetone by sonication. Five such cycles of precipitation in 100% acetone were carried out. The five supernatants, pooled together (after being filtered through a pipette plugged with cotton wool and dried), and the final pellet were examined for activity.

Capillary assay

Figure 1A:
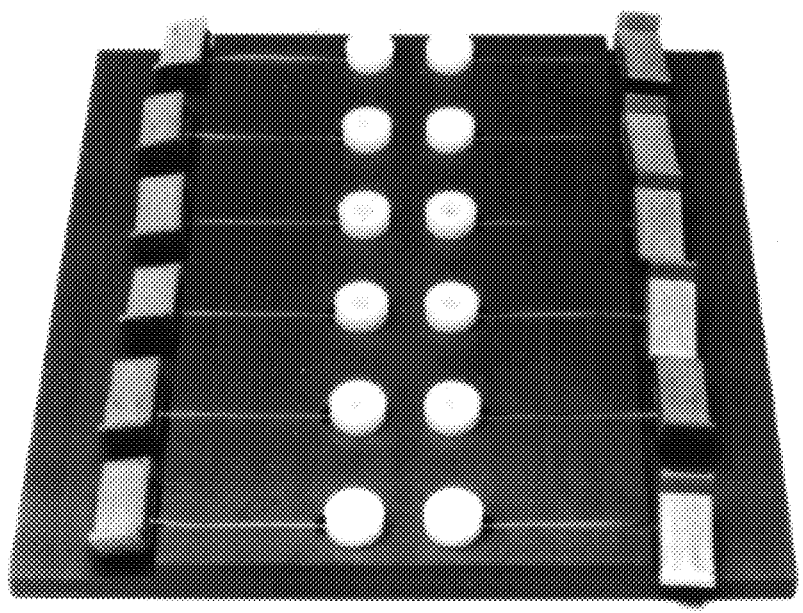
FIGS. 1A–B depict a multicapillary system for measuring chemotaxis. Panel A gives a top view of the system, and Panel B shows a vertical cross section of a Teflon well. The dimensions of the well are given in mm. The length of the polyethylene tubes ("capillaries") is 55 mm.
Figure 1B:
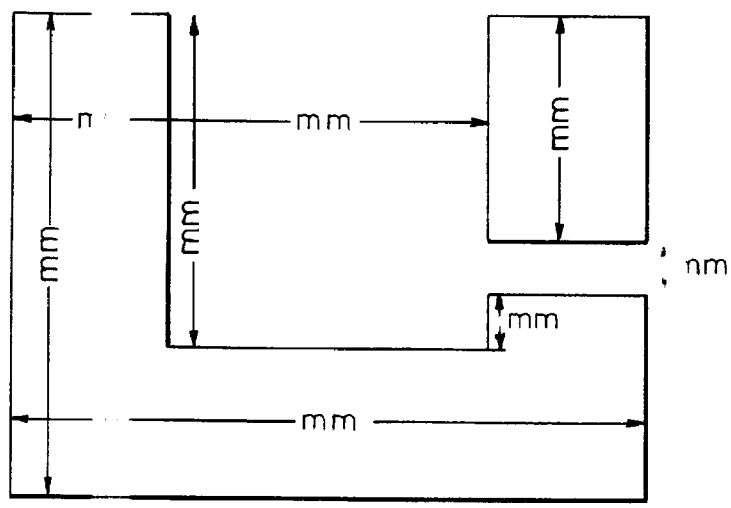

Capillary assays were carried out in a system consisting of a series of Teflon wells and polyethylene tubes (Intramedic Parsippany, N.J., PE-50, I.D. 0.058 mm, denoted herein in the specification as "capillaries") as shown in FIG. 1. (The use of polyethylene tubes, instead of glass capillaries, prevented adsorption of spermatozoa to the tubes). The wells were filled with 100 μl of spermatozoa at a concentration of $1-2 \times 10^7$ cells/ml suspended in BWW or in the test solution, as indicated. The capillaries were filled either with BWW or with the test solution and sealed at one end with a clamp. The open side of each capillary was inserted into the well and the whole tray was incubated, unless mentioned otherwise, for a period of 30 min, either in a 37° C. incubator under 5% $CO_2$ or at room temperature (22°–25° C.). [In a separate experiment we determined the diffusion time of a dye, Coomassie Brilliant Blue G (Sigma Chemicals, St. Louis), from the capillary into the well. A gradient of the dye was established in the well within minutes and persisted for at least 90 min.]. The distribution of spermatozoa in the capillary was not homogeneous, as the concentration was highest near the open end of the capillary and lowest near its sealed end. Therefore the total content of each capillary was counted and the average concentration of the spermatozoa in each capillary at the end of the incubation period was determined by one of the following means. (i) Direct counting. The contents of the capillary was transferred into an Eppendorf tube containing 5 μl of 8% glutaraldehyde in water and the spermatozoa were counted under the microscope by a haemocytometer. (ii) Enzymatic (endopeptidase) assay. The content of each capillary (about 10 μl) was transferred to a microtiter plate, followed by addition of 200 μl endopeptidase substrate (3-carboxypropanoyl-alanylalanyl-leucine-4-nitroanilide, 0.4 mM, supplemented with *Streptomyces griseus* aminopeptidase) in a solution of Tris-HCl (50 mM), NaCl (100 mM), and $CaCl_2$ (1 mM), final pH 7.5. The plate was incubated overnight at 35° C. and the absorbance at 405 nm (due to release of 4-nitroaniline) was measured by a Bio-Rad (Brussels, Belgium) microplate reader (model 450). Since the seminal fluid has a high level of endopeptidase activity, it is essential that the concentration of seminal fluid retained in the sperm suspensions after washings should be less than $10^{-5}$ of the original concentration.

Microscoipic assay

Figure 2:
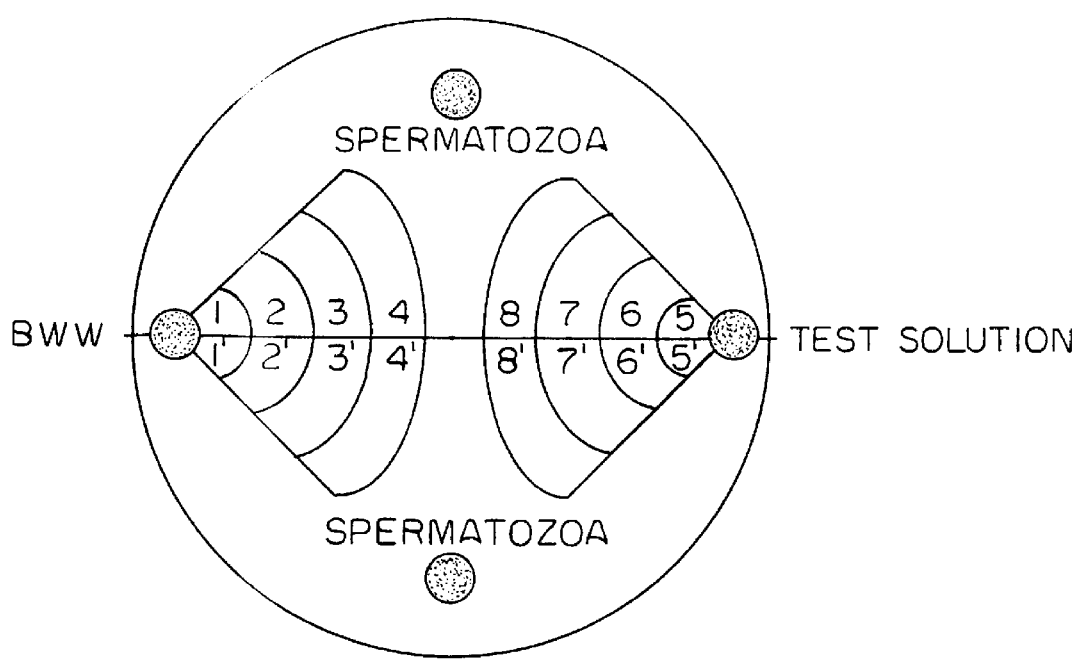
FIG. 2 shows the definition of zones in the sealed chamber in which were carried out microscopic assays of sperm chemotaxis.

Microscopic assays were carried out in a sealed chamber with a depth of 10 μm, so that the spermatozoa could only swim in two dimensions within the focal plane of a microscope throughout the observation period (Makler et al., 1992). The chamber contained four wells (black circles in FIG. 2), of which two opposing wells (top and bottom wells) were filled with washed spermatozoa, and the other two (left and right) were filled with the control and the test media, respectively. A gradient of the test solution was established by diffusion (Makler et al., 1992). The behavior of the spermatozoa in the chamber was recorded on video and then analyzed. The video recording commenced within 1 min after the chamber had been sealed and continued for 15 min. Although the observation field under the microscope was smaller than the field defined by the area between the four wells, we covered most of this area by recording two smaller areas (2.11 $mm^2$ each) in sequence. Each of these areas was divided into four serial zones. One area covered zones 1–4 (or 1'–4'), the areas of which were 0.22, 0.42, 0.62 and 0.85 $mm^2$, respectively, and the other one covered zones 5–8 (or 5'–8') (FIG. 2). The two areas were recorded alternatively for 10 s each time. The number of spermatozoa in each zone was counted in 30 s intervals, and the sperm density (number of spermatozoa per $mm^2$) was calculated.

Track analysis

The experiments for track analysis were carried out in two steps. First, in order to find out the time period in which the sperm accumulation in zone 5 was higher than in zone 1, a regular microscopic assay was carried out as described above. Then, two experiments were carried out, one for the analysis of spermatozoa near the follicular fluid-containing well (zone 5), and one for the analysis of spermatozoa near the BWW-containing well (zone 1). The experiments of this step were performed with only $(0.81) \times 10^8$ spermatozoa/ml (to avoid confusion between crossing tracks). At this sperm concentration the numbers of spermatozoa that reached zones 1 and 5 were 6–14 and 13–32, respectively (equivalent to 11–25 and 23–56 spermatozoa/mm$^2$). The video recording was carried out for 10 min without shifting the microscope from one well to another. The trajectories made by the swimming spermatozoa were obtained by backwards and forwards tracing of the video-recorded tracks of spermatozoa found in zones 1 and 5. The tracing was performed manually by drawing on transparencies. The starting point of each trajectory was its first appearance on the video screen. The trajectory ended either when the spermatozoa entered the well or when it left the video screen. Accordingly, the duration of the recorded tracks varied. The swimming speed of each spermatozoon was calculated for the period of time from its first appearance on the video screen until its entrance into zone 1 or 5.

Sperm separation procedures

Separation of spermatozoa according to their responsiveness was carried out in a conventional gradient maker Lucite apparatus consisting of two chambers (9.8 mm in diameter) connected by a tube (33 mm long, 2.8 mm in diameter). With the valve open, the connecting tube (200 $\mu$l in volume) was filled with BWW. The valve was then closed, and chamber no. 1 was filled with 1 ml spermatozoa (unless mentioned otherwise, $10^8$ cells/ml, suspended in BWW), and chamber no. 2 with 1 ml attractant diluted in BWW. On each day of experiment, the dilution of the attractive fraction of follicular fluid (the supernatant obtained after precipitation with 90% acetone, denoted hereafter as "attractant") was the dilution in which optimal accumulation was observed in the responsiveness assays of that day ($10^3$–$10^4$ fold dilution). The separation was initiated upon opening the valve. The apparatus was incubated at room temperature (21°–24° C.) for 60 min (unless mentioned otherwise), during which time a concentration gradient of the attractant was established by diffusion (and verified, in a parallel experiment, by monitoring of the time-dependent color change of phenol red in the apparatus following the addition of 0.1N HCl to one of the wells). The sperm suspensions from both chambers were collected and washed twice by centrifugation (120.g, 15 min). The original population was similarly washed as a control.

Example 1

Physiological Conditions for Detecting Sperm Accumulation in Follicular Fluid

One of the characteristics of our earlier measurements of sperm attraction or accumulation, which employed a 48-well chemotaxis chamber (Gnessi et al., 1985), was a small signal and a large standard deviation, for which reason a large number of experiments was required to obtain statistically significant results (Ralt et al., 1991). In the present application, we initially wished to determine whether the low signal-to-noise ratio in our assays was a reflection of a non-optimal assay, non-optimal experimental conditions, or an intrinsic physiological property of the spermatozoa.

a. Capillary assays with an ascending gradient of follicular fluid

Figure 3:
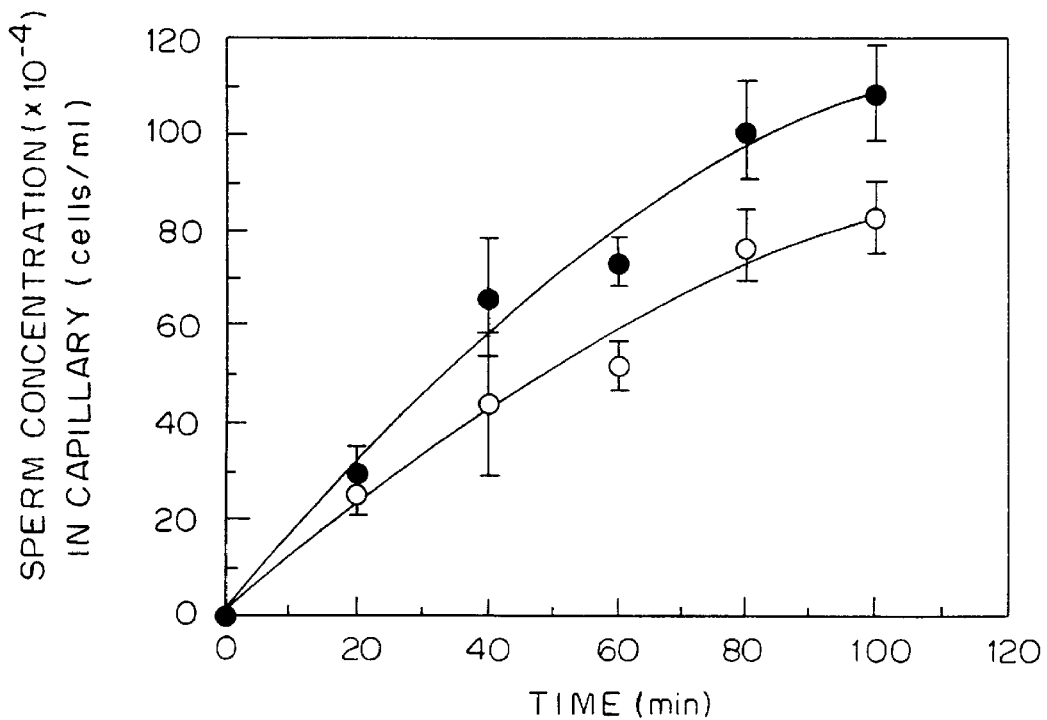
FIG. 3 shows time-dependent accumulation of spermatozoa in the polyethylene capillaries. The figure contains the results of a typical experiment carried out as described in Materials and Methods. Each well contained preincubated spermatozoa, suspended in Biggers, Whitten and Whittingham (BWW) medium ($2 \times 10^7$ cells/ml). The capillaries contained either 3,000-fold diluted follicular fluid in BWW (filled circles), or just BWW (empty circles). The number of spermatozoa (determined by direct counting) that migrated into the capillaries within the indicated period of time is shown. Each point represents the average of 6 determinations±S.D.
Figure 4:
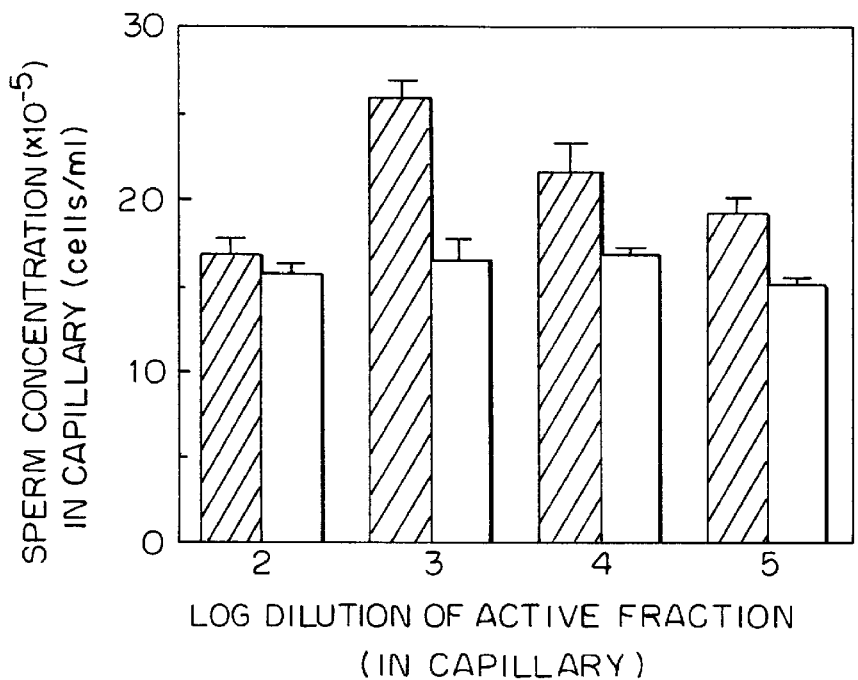
FIG. 4 shows concentration dependence of sperm accumulation in capillaries containing an active fraction of follicular fluid. The assays were carried out at room temperature (25° C.). The active fraction of follicular fluid was prepared by 90% acetone precipitation as described in Materials and Methods and diluted in BWW to the extent indicated in the figure. The figure contains the results of a single experiment (out of 11 in total). Each point represents the mean of 6 capillaries±SEM (standard error of the mean) (SEM, rather than S.D., is shown here in order to make easier the comparison with FIG. 1 of Ralt et al., 1991). The number of spermatozoa in the capillaries was determined by direct counting. Hatched columns, active fraction in the capillary; empty columns, BWW in the capillary.

To address the first possibility and to try to increase the signal-to-noise ratio, we tested a number of different assays, configurations, and techniques. The best results were obtained with the system shown in FIG. 1 consisting of spermatozoa in Teflon wells and various dilutions of follicular fluid in capillaries. FIG. 3 shows the time-dependent accumulation of spermatozoa in an active follicular fluid [3000-fold diluted, the activity of a follicular fluid defined herein as its ability to attract spermatozoa (Ralt et al., 1991)]. When compared with previous studies, in which a 48-well chemotaxis chamber was used (Ralt et al., 1991), the standard deviation in this assay was indeed lower. However, the signal (i.e., the ratio or the difference between the follicular fluid-containing capillaries and BWW-containing capillaries) was as low as before [cf. FIG. 1 in ref. (Ralt et al., 1991)] and its magnitude did not depend on the temperature in the range 25°–37° C. With all the techniques tested by us, including this assay, there was a large variability in the degree of activity among the tested follicular fluids (all derived from follicles containing fertilizable eggs); a few follicular fluids had no detectable activity at all. Hereafter, we pre-tested only follicular fluids by the capillary assay and used only the active fluids. The dependence of the sperm accumulation on the concentration in the capillaries of the follicular fluid's active fraction (described in the section (b) below), is shown in FIG. 4. The dependence was bell-shaped, typical of chemotaxis.

b. Optimizing the sperm parameters

Figure 5:
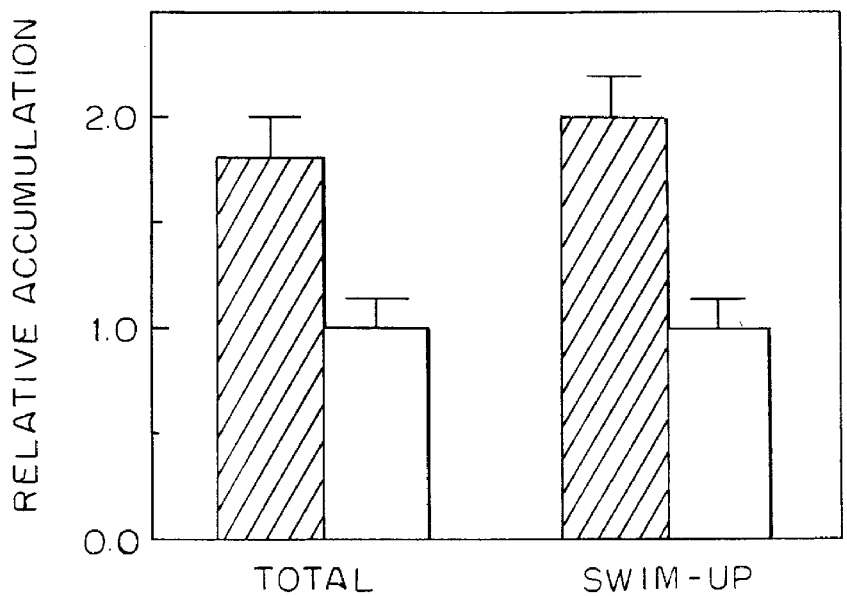
FIG. 5 shows accumulation assay of the swim-up fraction and the total population of spermatozoa. The swim-up fraction was isolated as previously described in Ralt et al., 1991. The experiment was carried out as described above in FIG. 3, except that the wells contained $1.5 \times 10^7$ cells/ml and the duration of the assay was 40 min. The total population was pre-washed and incubated for 2 h at 37° C. in 5% $CO_2$ incubator as was the swim-up fraction. Both sperm populations were normalized according to the accumulation of spermatozoa in BWW. Relative accumulation is defined as the ratio between the number of spermatozoa accumulated in the capillary and the average accumulation in the control of the same experiment (BWW in both the well and the capillary). The number of spermatozoa in each capillary was estimated by the endopeptidase enzymatic assay. The data shown are of a representative experiment (out of 5 in total).

Since the assay was not the cause of the low signal-to-noise ratio, we examined whether or not the experimental conditions were the cause. In our earlier studies we used only "swim-up" spermatozoa (i.e. highly-motile spermatozoa collected from the upper layer of a suspension that had not been stirred for 2 h) (Ralt et al., 1991), as for current procedures of in vitro fertilization (Dandekar and Quigley, 1984). In the present experiment, we used the total sperm population rather than the swim-up subpopulation, as we observed that the responses of the two populations were similar (FIG. 5). Since spermatozoa are known to undergo a time-dependent process of capacitation (Florman and Babcock, 1991), we incubated the total sperm population for different periods of time and measured their responsiveness to follicular fluid. As shown in FIG. 6, sperm incubation was a prerequisite for observing sperm accumulation in follicular fluid. These results suggest that spermatozoa undergo some physiological change, possibly capacitation, before they can respond to follicular fluid. Capacitation involves functional changes undergone by mammalian spermatozoa during their passage through the female genital tract which enable them to penetrate the ovum. Capacitation is an obligatory requirement for the spermatozoa to be able to undergo the acrosome reaction, which is a series of distinct membrane changes that enables the spermatozoa to penetrate the egg (Florman and Babcock, 1991). Sperm capacitation can occur either in the female reproductive tract or in vitro, by incubation of spermatozoa washed off the seminal fluid for at least 30 min at room temperature or above.

We also examined the temperature effect on sperm accumulation in follicular fluid and found that the accumulation was similar both at room temperature and at 37° C.

The observation in all of our assays, even under optimal experimental conditions, of low signals and varied follicular fluid activities, indicated that the cause of the low signal and the varying activity is physiological rather than technical. The main physiological reason is probably the responsiveness of only a fraction of the sperm population to follicular factor(s) (as shown below in Example 4).

Example 2

Determination of the Mechanism of Sperm Accumulation in Follicular Fluid

Having optimized the experimental conditions (with respect to the assay, temperature, and sperm incubation time), we examined what processes are involved in sperm accumulation. In principle, apparent sperm accumulation in capillary assays could result from chemotaxis, chemokinesis, or trapping (Eisenbach et al., 1992; Ralt et al., 1991). [Trapping may result from a negative effect of follicular fluid on motility, from a change in swimming behavior at a particular concentration of follicular fluid (distinct from chemotaxis, where the change in swimming behavior is in response to a gradient of a chemical), from mechanical effects such as adsorption to glass or capillary, or from any combination thereof]. To distinguish between chemotaxis, chemokinesis, and trapping, we carried out a variety of assays, both macroscopic and microscopic.

a. Capillary assays with a descending gradient of follicular fluid

Distinction between these processes is difficult because of the low signal. Therefore, we carried out assays in which the direction of the chemotactic effect was opposite to that of the chemokinetic effect, and in which trapping (if it occurs) would affect both processes similarly. In other words, rather than measuring the tendency of the spermatozoa to accumulate in follicular fluid, as in the experiments shown in FIGS. 3 and 4, we measured their tendency to leave the follicular fluid. The spermatozoa in the wells were suspended in follicular fluid, and the capillaries contained either BWW (Table 1, setting no. 1) or follicular fluid (setting no. 2). In the former setting, the spermatozoa in the well sensed a descending gradient of follicular fluid as they moved to the capillary; in the latter setting they sensed no gradient at all. A control for lack of gradient in the absence of follicular fluid was also carried out (setting no.3). The concentration dependence of the sperm accumulation in these settings is shown in FIG. 7. The results suggest that both chemotaxis and chemokinesis occur. Chemotaxis is suggested by the lower accumulation in the capillary under conditions of a descending gradient of follicular fluid vs. no gradient at all (setting no. 1 vs. no. 2). Chemokinesis is manifested by the higher number of spermatozoa that reached the capillary when both the well and the capillary contained follicular fluid vs. when both of them contained just BWW (setting no. 2 vs. 3). Trapping as a sole cause may be ruled out because the spermatozoa in settings nos. 1 and 2 were already suspended in the "trap" (i.e. in follicular fluid) prior to the assay.

Table 1

Sperm accumulation in capillary assays with a descending gradient of follicular fluid or no gradient at all.

| Setting no. | Follicular fluid[a] in well | capillary | Relative sperm accumulation in capillary[b] |
|---|---|---|---|
| 1 | + | − | 1.05 ± 10.11 |
| 2 | + | + | 1.69 ± 0.16 |
| 3 | − | − | 1.00 ± 0.05 |

[a]The follicular fluid was 1000-fold diluted.
[b]Relative accumulation is defined as the ratio between the number of spermatozoa accumulated in the capillary and the average accumulation in the control of the same experiment (BWW in both the well and the capillary). Each well contained 1.5 × $10^7$ spermatozoa/ml. The assays were carried out at 37° C. for 40 min. Each result represents 36 determination (3 donors of spermatozoa; 2 experiments with each donor; 6 capillaries in each experiment) ± SEM. The number of spermatozoa in the capillaries was determined by direct counting. The two-way factorial ANOVA test showed no significant interaction between the donors and the settings. The P value for the settings was 0.0001. According to the Fisher test, the differences between setting no. 1 vs. no. 2 and between no. 2 vs. no. 3 were significant at the 99% level.

b. Capillary assays with spermatozoa having exceptionally high motility

To determine unequivocally whether or not chemotaxis occurred on top of the chemokinetic effect seen in Table 1, we repeated the experiments with a follicular fluid and with an active fraction thereof (obtained by 90% acetone precipitation), but this time using spermatozoa from sperm donations with exceptionally high motility. [The motility of washed spermatozoa was measured by capillary assays in which both the well and capillary contained BWW (i.e., like setting no. 3 in Table 1). The criterion for exceptionally high motility was that more than 10% (e.g., 15–25%) of the spermatozoa in the well accumulated within 1 h in the capillary. (The accumulation level of spermatozoa with regular motility varies between 1 to 10%)]. We observed that the motility of such spermatozoa cannot be further enhanced by either follicular fluid or drugs that normally stimulate sperm motility (e.g., caffeine). Table 2 contains the results of two typical experiments of this kind. Even though the chemokinetic effect was very small or even non-existent with such spermatozoa (setting no. 2 vs. no. 3), their accumulation in the capillaries under conditions of a descending gradient of follicular fluid vs. no gradient at all was significantly lower (setting no. 1 vs. no. 2). This observation, made in the absence of chemokinesis, provides a strong evidence in favor of the occurrence of chemotaxis.

TABLE 2

Capillary assays with spermatozoa having exceptionally high motility

| Setting no. | Follicular fluid or active fraction in[a] well | capillary | Relative sperm accumulation in capillary[b] follicular fluid | active fraction |
|---|---|---|---|---|
| 1 | + | − | 0.57 ± 0.04 | 0.71 ± 0.03 |
| 2 | + | + | 1.11 ± 0.04 | 0.97 ± 0.07 |
| 3 | − | − | 1.00 ± 0.04 | 1.00 ± 0.04 |

[a]The follicular fluid and active fraction were $10^4$-diluted and $10^3$-diluted, respectively.
[b]The experiments were carried out as in Table 1. The numbers are the mean ± SEM of 6 determinations in each experiment. The difference between settings 1 and 2 was statistically significant (P<0.003 according to Student's t-test); it was not significant between settings 2 and 3.

c. Sperm accumulation in a sealed chamber

We followed microscopically the response of spermatozoa to a spatial gradient of follicular fluid in a sealed chamber that had been developed for this purpose ([Makler et al., 1992]; FIG. 2). As shown in FIG. 8, the number of spermatozoa near the follicular fluid-containing well was 1.3-fold to—2.2 fold higher than near the BWW-containing well which was free of follicular fluid. All the spermatozoa seen in the chamber were motile. These results are in line with sperm chemotaxis; if the only effect of follicular fluid on spermatozoa had been enhancement of motility, the accumulation near the follicular fluid-containing well would be expected to be lower than near the control well. As before, the difference between the sperm numbers near the wells was not dramatic. This is not surprising in the light of our finding that, at a given time, only a small fraction of the sperm population responds to follicular fluid (see below). In this assay, as in the capillary assay, the correct dilution of follicular fluid was essential.

The time-dependence distribution of the spermatozoa in the sealed chamber is shown in FIG. 9 for the active fraction of follicular fluid. When the content of both wells was identical [either BWW (FIG. 9A) or follicular fluid (not shown)], the numbers of spermatozoa near each of the wells were similar. When the content of the wells was different, the sperm density near the well with the active fraction was higher from the very beginning. In accordance with the diffusion of the active fraction from the well, the difference was the largest and first apparent between zones 5 and 1 (closest to the wells); in the more remote zones, the difference was smaller and apparent at later stages (FIG. 9B).

d. Sperm trajectories in a gradient of follicular fluid

Chemotaxis, unlike chemokinesis and trapping, is expected to involve typical directional changes of the spermatozoa towards the source of the attractant. We therefore compared the trajectories of the spermatozoa found near the well containing the active fraction (i.e. the test well containing the presumed attractant), with those found near the BWW-containing well (the control well). Various patterns of trajectories were observed, which were categorized by us into 4 groups. Representative examples of these groups observed near the test and control wells are shown in FIG. 10A and 10B, respectively. The prevalence of each group, as well as its average swimming speed, is shown in Table 3. The following conclusions could be drawn from the figure and table. (i) A significantly larger number of spermatozoa exhibited distinct directional changes towards the test well than towards the control well (Table 3, category 1). (ii) Within this category, there were marked differences between the trajectories near the test and control wells; the trajectories approaching the test well had more frequent and sharper directional changes (panel A vs. panel B in FIG. 10). This is further demonstrated in FIG. 10C, which includes additional typical trajectories of category-1 spermatozoa near the test well. Of the spermatozoa approaching the test well, 84% acquired, near the well, motility patterns resembling hyperactivation (e.g., wide amplitude and marked lateral displacement of the head (Yanagimachi, 1970 and Burkman, 1990)) (FIG. 10A); none acquired hyperactivation-like motility near the control well (FIG. 10B). (iii) Some spermatozoa exhibited distinct directional changes towards the wells but left the zone after a while (Table 3, category 2); most of the spermatozoa belonging to this category spent more time near the test well (FIG. 10A) than near the control well (FIG. 10B). Again, 69% of the spermatozoa of this category acquired hyperactivation-like motility near the test well but none did near the control well. (iv) Hyperactivation-like motility was also observed in the other categories (71–80%), but only near the test well (FIG. 10). These results are in line with sperm chemotaxis and with the notion that, at any given time, only a small fraction of the sperm population is responsive. Table 3. Pattern types of trajectories made by spermatozoa entering zones 1 or 5

| Behavioral Spermatozoa entering zone #1 (BWW) | | | Spermatozoa entering zone #5 (active fraction) | |
|---|---|---|---|---|
| category[a] | %[b] | Swimming speed[c] | % | Swimming speed |
| 1 | 12 | 44 ± 7 | 21 | 51 ± 14 |
| 2 | 7 | 46 ± 7 | 15 | 48 ± 13 |
| 3 | 36 | nonapplicable | 38 | nonapplicable |
| 4 | 45 | 47 ± 12 | 26 | 47 ± 12 |

[a]The categories (cf. FIG. 10) are: 1 - distinct directional changes towards the well; 2 - as category 1, but the spermatozoa did not stay near the well (i.e., they left zone 1 or 5); 3 - trajectories of spermatozoa which, at the moment of the initiation of video recording, were close to or already in zone 1 or 5; and 4 - the rest of the trajectories.
[b]The total numbers of trajectories analyzed (100%) were 42 and 89 for zones 1 and 5, respectively. The sample size was chosen as such that the average would not change upon further increase in the number of tracks analyzed.

-continued

| Behavioral Spermatozoa entering zone #1 (BWW) | | | Spermatozoa entering zone #5 (active fraction) | |
|---|---|---|---|---|
| category[a] | %[b] | Swimming speed[c] | % | Swimming speed |

[c]The swimming speed (in μm/s) was calculated for the section of the trajectory out of zone 1 or 5 and is the mean ± S.D. of all the trajectories of the category.

Example 3

Isolation of the chemotactic factors by fractionation of follicular fluid

From the above experiments it appeared that, under well-controlled conditions, sperm attraction can be observed and that this attraction is the result of chemotaxis and chemokinesis and, ultimately, hyperactivation-like motility. At this stage we initiated studies towards the identification of the attractant(s), denoted herein as chemotactic factors, in the follicular fluid.

a. Precipitation by 90% acetone

The proteins of the follicular fluid were precipitated with 90% acetone and chemotactic and chemokinetic activities were examined in the pellet and in the supernatant fractions following evaporation of the acetone. FIG. 11 shows the results of capillary assays which indicate that both the chemotactic and chemokinetic activities are found only in the supernatant. This was confirmed by microscopic assays (FIG. 9). The specific chemotactic and chemokinetic activities (per protein content) of the supernatant were >60 fold higher than those of the original follicular fluid and both were concentration-dependent (FIG. 7).

b. HLPC size-exclusion column

Dried supernatants obtained from the 90% acetone precipitation of several follicular fluids were pooled and resuspended in 100 mM or 10 mM phosphate-buffered saline (PBS) pH 7.4. The suspension was centrifuged for 5 min and filtered through a cotton wool plugged-tip in order to remove undissolved particles. The filtrate was applied to a size-exclusion HPLC Bio-Sil TSK-125 column (7.5 mm×600 mm, BIO RAD), which has a hydrophilic bonded phase silica G2000 SW packing with a pore size of 125 angstroms and a particle size of 10±2 μm, utilizing HP 1040 A diode array chromatography detection system and Waters HPLC system composed of two pumps (Model 510) and an automatic controller. This HPLC technique is considered a high resolution analytical technique for peptide analysis. The separation was carried out at room temperature using PBS (100 mM or 10 mM at pH 7.4) as the elution buffer. The 40 fractions eluted from the column were kept at 4° C. until use. In order to facilitate the identification of active fractions, a part of each of the 40 fractions was lyophilized and resuspended in 20 μl of assay buffer. Every 10 to 20 fractions were pooled together and assayed for biological activity. The active pools were divided into subpools and the procedure was repeated for the active sub-pools. Finally, two different fractions out of the forty were found to be active: a fraction eluted at 17.0–17.5 min (corresponding to molecular size of 13±1 kDa) and a fraction eluted at 25.0–25.5 min (after 1.3 kDa marker and after sodium azide, thus corresponding to an apparent molecular size of <1.3 kDa) (FIG. 12). The <1.3 kDa fraction contained 10 μg/ml protein while the 13 kDa fraction contained 15 μg/ml protein estimated by fluorescamine using BSA as a standard. The specific activities of the <1.3 kDa and the 13 kDa fractions increased 23 and 19 fold, respectively, compared to the supernatant Table 4).

The peak of chemotactic activity of the <1.3 kDa fraction, as measured by the microscopic assay, was observed in $10^6$ dilution. The peak of activity of the 13 kDa fraction was observed in $10^5$ dilution (FIG. 13).

TABLE 4

The enrichment achieved by acetone precipitation and HPLC purification

| Preparation | Specific chemotactic activity (relative units) |
| --- | --- |
| Follicular fluid | 1.0 ± 0.6 |
| Acetone (90%) supernatant | 90 ± 29 |
| Size exclusion fraction <1.3 kDa | 2,100 ± 900 |
| Size exclusion fraction 13 kDa | 1,700 ± 2000 |
| Reversed-phase fraction <1.3 kDa | 18,000 ± 2000 |
| Reversed-phase fraction 13 kDa | 53,000 ± 3000 | c. HPLC reversed-phase column

The two active fractions obtained from the size-exclusion column were applied separately to a reversed-phase-C18 column (4.5 mm×100 mm, Sota flow, Japan) using the HPLC system as described above. This column separates according to hydrophobic properties of the substances. The effluent was monitored by absorbance at 215 nm. In general, the separations were carried out using the following program: 100% solvent A (0.1% trifluoroacetic acid (TFA) in water) for 10 min and a linear gradient from 0 to 10% solvent B (0.1% TFA in acetonitrile) over the next 15 min. Over the next 25 to 40 min a gradient from 10 to 80% solvent B was developed. The flow rate was kept at 0.25 ml/min. As with the size-exclusion column, in order to facilitate the identification of the active fraction(s), pooled fractions were assayed for chemotactic activity, and the active pool was then sub-pooled. The activity of the 13 kDa factor was found to be eluted at 20% acetonitrile (fractions #33–34) (FIG. 14), and the activity of the <1.3 kDa factor was eluted at 0% acetonitrile (fractions #6–8) (FIG. 15). The relative chemotactic activity of fractions #33–34 and #6–8 (as measured by the microscopic assay) was 1.8 and 1.9, respectively (FIG. 23). While the activity of the 13 kDa factor correlated with a small elution peak (on the shoulder of another peak) at 33–34 min (FIG. 14), the <1.3 kDa factor was associated with a distinct elution peak at 7–9 min (FIG. 16). Both the <1.3 kDa and 13 kDa fractions had absorbance peaks at 215 nm and 280 nm (FIG. 16).

The following approaches were designed to get further purification of the <1.3 kDa factor.

d. Ion-exchange column

In order to eliminate small molecules that might be coeluted with the active peak (<1.3 kDa) of the reversed-phase column, the peak was applied onto a cation-exchange column (4 mm×150 mm, Pickering) utilizing Dionex chromatography system. The separation was carried out using the following program: 100% buffer A (NaCitrate, 0.2N, pH=3.15) over the first 29 min. A linear gradient was developed from 0% buffer A to 100% buffer B (NaPhosphate, 1N, pH=7.4) over the next 29 to 54 min. A linear gradient was also developed from 85% buffer B to 15% buffer C (NaOH, 0.5N, pH=12) between 54 to 72 min. The flow rate was kept constant at 0.4 ml/min. After dividing the 72 fractions eluted from the column into pools and sub-pools thereof, the chemotactic activity was checked using the microscopic assay. Out of these 72 fractions, two consecutive fractions eluted close to the void volume were found to be active. The activity was associated with an absorbance peak at 520 nm following a reaction with ninhydrin, indicating the presence of amino or imino groups.

Dose-response experiments (microscopic assays) of the active fractions obtained in the different fractionation steps showed a maximal relative activity (per volume) at the dilution of $10^5$–$10^6$. A point worth mentioning is that these relative activities were almost constant (1.6–1.9) throughout the purification steps (FIG. 23). The reason is that the relative activity (unlike the specific activity) reflects the fraction of responsive spermatozoa and is not dependent on the purity of the chemotactic factor.

e. Thin layer chromatography

This method was undertaken to examine the degree of purification of the <1.3 kDa factor and as a final separation step. At first, the reversed-phase peak was applied to silica gel 60 $F_{254}$ (50 mm×75 mm, 0.2 mm thick) with water as the mobile phase, since the previous results suggested that the factor is probably hydrophilic (eluted at 0% acetonitrile). Two spots were visualized by inspection with a short wavelength UV lamp. One of them migrated to the front of the silica gel and the second one was the non-mobile substance. In order to prevent the first spot from reaching to the front of the silica gel, a less polar solvent, ethanol, was used as the mobile phase. The active peak eluted from the reversed-phase column was applied to the silica gel under these conditions. Again, two spots were visualized by inspection with a short wavelength UV lamp (FIG. 17). Using ether or acetone as the mobile phase did not separate the reversed-phase fraction on the silica gel.

For analyzing the activity, the two spots observed in FIG. 17 were removed from the plate and extracted with 99.8% ethanol. Then, each tube was centrifuged for 3 min. The supernatants were evaporated under a nitrogen stream, dissolved in BWW and analyzed for activity using the microscopic assay. The relative chemotactic activities of the mobile spot and non-mobile spot were 1.83 and 1, respectively, indicating that the chemotactic factor was in the mobile spot. A relative chemotactic activity of value 1 means no activity.

f. Characterization of the chemotactic factors (i) Proteolytic resistance

In order to examine whether the active factors contain peptide bonds sensitive to proteolytic digestion, the supernatant of the 90% acetone precipitation and the <1.3 kDa and 13 kDa factors, eluted from the reversed-phase column, were tested for their resistance to Pronase E (Sigma) treatment. The factors, 1:10 diluted, were incubated at room temperature for 3 hours with 20 μg of enzyme dissolved in 95 mM NaCl, 4.8 mM KCl, 1.3 mM $CaCl_2$, 1.2 mM $KH_2PO_4$, 1.2 mM $MgSO_4$, and 25 mM $NaHCO_3$ (pH 7.4). The control mixture was also dissolved in this buffer but without the enzyme. After incubation, the reaction mixture was placed in the microscopic chamber in order to analyze the chemotactic activity. To eliminate the possibility that Pronase-E affects the assay, the chemotactic activity was compared to buffer which was also treated with this enzyme. Furthermore, in a separate experiment, in which pronase was incubated with the spermatozoa, pronase was found to have no effect on the spermatozoa. Dose response experiments showed that both pronase-treated factors, unlike the non-treated factors, lost their activity as a result of the treatment (FIG. 18), thus indicating that they are, at least in part, of peptidic nature.

(ii) Precipitation with 100% acetone

In order to characterize the hydrophobicity/hydrophilicity of the chemotactic factors, the dried 90% acetone supernatant was reprecipitated by 100% acetone. This acetone had been preincubated with hygroscopic molecular sieve beads overnight in order to eliminate traces of water. The suspension was sonicated vigorously for 1 min and incubated for 1 hour at 0° C. Five such cycles were repeated, each time the supernatant was filtered through a cotton-wool plugged pipette. The pooled supernatant was evaporated and reconstituted with water to the volume of the original 90% acetone-supernatant. The relative chemotactic activity as measured by the microscopic assay was predominantly in the pellet, thus confirming the hydrophilic nature of the chemotactic factors.

Example 4

Chemotactic responsiveness by human spermatozoa

The previous examples have shown that human spermatozoa respond to follicular fluid by attraction to chemotactic factor(s) in the fluid, accompanied by enhancement of motility and ultimately hyperactivation. In order to quantitate the sperm response, spermatozoa were exposed to a gradient of chemotactically-active fraction of follicular fluid, and separated between the spermatozoa which accumulated in the attractant and those which were not. Two subpopulations were thus obtained: one enriched with chemotactically-responsive spermatozoa, and one deficient in such spermatozoa. The fraction of the responsive spermatozoa out of the total sperm population was 2–12% at any measured time point. With time, the responsive spermatozoa lost their ability to be attracted, while such activity was gradually acquired by the subpopulation originally deficient in responsive spermatozoa. These results indicate that the identity of the responsive spermatozoa is continuously changing. If the in vitro results are representative of the physiological conditions in vivo, it implies that the role of sperm chemotaxis combined with enhanced motility may be to select capacitated spermatozoa and bring them to the egg. Such a mechanism may increase, over an extended period of time, the prospects that an egg will meet capacitated spermatozoa as soon as it ovulates.

a. Sperm Separation into Sub populations

To examine the possibility that not all spermatozoa can simultaneously respond to follicular factors, it was first attempted to separate between the responsive and nonresponsive spermatozoa, as described in Materials and Methods. Follicular fluid served as a source of soluble factors that might be secreted from the egg or its surrounding cells. As a control and as a means of distinguishing between attraction and coincidental arrival, the separation procedure was repeated, with BWW replacing the attractant in chamber no. 2. Various separation periods were tested and, as shown in FIG. 19, at any time period more spermatozoa reached chamber no. 2 when it contained attractant than when it contained BWW. From this ratio the extent of enrichment with responsive spermatozoa was calculated, indicating that the shorter the separation time, the higher was the enrichment (e.g. at 15 min the number of spermatozoa that passed to chamber no. 2 when it contained the attractant was twice the number that passed when it contained BWW; at 60 min the ratio was 1.3 only). Nevertheless, in order to optimize between reasonable enrichment, on the one hand, and a number of spermatozoa in chamber no. 2 which would be sufficiently large for testing their responsiveness, on the other hand, we chose 60 min as the separation time in our next experiments. During this separation period, an average of 28±3% (means±S.D. for all the experiments included in Table 5) of the spermatozoa in chamber no. 1 moved to chamber no. 2 when the latter contained the attractant. In all the experiments, the number of spermatozoa that passed to chamber no. 2 when it contained the attractant, was larger than the number which passed when the chamber contained BWW. The difference at 60 min was 4±3% (mean±S.D.) of the original sperm population. The range of the difference, at any time point, was 2–12%. This indicates that about 2–12% of the spermatozoa in the original sperm population were responsive.

TABLE 5

Relative responsiveness of the separated subpopulation

| Separation Procedure | Relative responsiveness[a] of the populations ± SEM | | | F-test[b] | n[c] | P value[d] |
|---|---|---|---|---|---|---|
| | Original | Passed | Remaining | | | |
| Attractant | 1.82 ± 0.13 | 2.13 ± 0.16 | 1.28 ± 0.05 | 14.5 | 12 | 0.0001 |
| BWW | 1.94 ± 0.22 | 1.40 ± 0.08 | 1.66 ± 0.14 | 3.3 | 7 | 0.072 (insignificant) |

[a]The relative responsiveness was calculated as the ratio between the maximal sperm densities in the right half (comprising the attractant-containing well) and the left half (BWW-containing well) of the device, integrated over the whole observation period (10 min).
[b]The statistical significance was calculated by ANOVA with repeated measures.
[c]n, The number of experiments. The experiments were carried out with 3 sperm donors and active fractions from 6 follicular fluids.
[d]The P value refers to the original, passed, and remaining populations together, as calculated by ANOVA.

b. Responsiveness of the Separated Subpopulations

To examine whether the separation indeed resulted in two different subpopulations, one enriched and one deficient in responsive spermatozoa, the responsiveness of each subpopulation was determined and compared to that of the original population (Table 5). The sperm suspension collected from chamber no. 2 (attractant-containing) displayed higher responsiveness than that of the original sperm population. On the other hand, the remaining sperm suspension collected from chamber no.1 was significantly less responsive. Such statistically-significant differences in responsiveness, either between the separated subpopulations or between them and the original population, were not observed when the separation had been carried out, as a control, with BWW substituting for the attractant (Table 5). To rule out the possibility that the observed increase in the sperm responsiveness is the consequence of the sperm incubation with the attractant, we incubated the original spermatozoa with the attractant (diluted as in the separation procedure) and then washed them and re-examined their responsiveness to it. As shown in FIG. 20, the incubation with the attractant (unlike incubation in the absence of the attractant), not only did not increase the sperm responsiveness but it had a negative effect on it. The above results indicate that the spermatozoa collected from chamber no. 2 were indeed enriched with responsive spermatozoa whereas those collected from chamber no. 1 were deficient in responsive spermatozoa.

c. Sequential Acquisition of Sperm Responsiveness

To determine whether the identity of the responsive spermatozoa is constant or changing, we studied the responsiveness of the original population and its subpopulations as a function of the time after separation. As shown in FIG. 22, the passed subpopulation had very little responsiveness left at 100 min after the separation (i.e., 50 min after the first measurement). At the same time, the remaining subpopulation acquired responsiveness which reached a value close to that of the original sperm population. Interestingly, in spite of these changes in the responsiveness of the subpopulations, the responsiveness of the total population as a whole remained essentially unchanged. These results point to a continuous process of replacement of responsive spermatozoa within a sperm population.

The results of this example demonstrate that in humans, unlike in organisms in which the fertilization is external, only a fraction of the spermatozoa at a given time are responsive to the attractant. They further show that the identity of the responsive spermatozoa changes with time: responsive spermatozoa lose their activity while others acquire it.

d. Correlation Between Sperm Capacitation and Chemotaxis

To investigate whether the chemotactic spermatozoa are capacitated, we first separated the chemotactic spermatozoa from the rest of the sperm population and then analyzed all the sperm populations for capacitation.

We used as a capacitation probe the fluorescent lectin fluorescein-iso-thiocyanate concanavalin A (FITC-Con A). The fluorescence patterns of human spermatozoa labeled with this probe are known to change during incubation in vitro, i.e., during capacitation. Thus, capacitated spermatozoa are uniformly stained at the periphery of the sperm head, and the percentage of spermatozoa exhibiting this pattern increases during the incubation. Other spermatozoa, both acrosome-reacted and intact, have polar staining: acrosome-reacted spermatozoa are stained from the equatorial region and down towards the tail, whereas intact cells are stained at the distal part of the head. To determine whether the presumed capacitation-related pattern is indeed correlated to capacitation, we carried out the following experiment. Since phorbol ester (TPA) is known to induce the acrosome-reaction in capacitated spermatozoa only, we compared the fluorescence pattern of a total TPA-stimulated sperm population with that of non-stimulated spermatozoa. The sperm population was stained with either rhodamine-Con A or FITC-*Pisum sativum* agglutinin (PSA, known to differentiate between intact and acrosome-reacted spermatozoa (Tesarik et al., 1993). The results obtained from two experiments (means±S.D.) are summarized in Table 6.

TABLE 6

Effect of TPA on capacitated spermatozoa

| Acrosome-intact | Capacitated | Acrosome-reacted | Treatment |
|---|---|---|---|
| 78% ± 0% | 12% ± 3% | 10% ± 3% | rhodamine-Con A |
| 73% ± 10% | 3% ± 1% | 19% ± 1% | TPA + rhodamine-Con A |
| 90% ± 6% | | 10% ± 6% | FITC-PSA |
| 83% ± 4% | | 17% ± 4% | TPA + FITC-PSA |

These results show that most of the presumably-capacitated spermatozoa indeed turned to be acrosome-reacted spermatozoa upon treatment with TPA, indicating that this fluorescent pattern indeed correlates with capacitated spermatozoa.

Using FITC-Con A, we found that the fraction of capacitated spermatozoa in the subpopulation separated by chemotaxis was higher than in the original population, whereas the fraction of capacitated spermatozoa in the remaining subpopulation was lower. This is shown in Table 7 for a typical experiment and in Table 8 for all the experiments carried out. This indicates that chemotaxis selets capacitated spermatozoa. Spermatozoa (45 μl of 100×10$^6$ cells/ml) were washed in a BWW medium (without glucose and BSA) and then cooled on ice for 10 min. 5 μl of 1 mg/ml of FITC-Con A was added and the mixture incubated for 30 min on ice. Sperm were then washed and fixed, on ice, with 2% formaldehyde for 30 min. An aliquote of the sperm suspension was dried on a microscope slide and was then covered with a droplet of PBS and a cover glass. The cover glass was sealed with a nail polish to avoid evaporation and the slides were incubated in dark at 4° C. The slides were inspected using a Zeiss Axiovert 35 microscope equipped with x63 oil objective. The fluorescein fluorescence was visualized using a 590 nm emission filter. 50 cells were inspected in each slide.

These findings, made in vitro, are indicative of what might be occurring in vivo. They suggest that spermatozoa in the female genital tract undergo a continuous process of acquiring and losing responsiveness to the attractant, so that there is always (i.e., throughout the lifetime of spermatozoa in the female genital tract) a sufficient number of responsive spermatozoa "on call", ready to be attracted to the egg as soon as it ovulates. Accordingly, since the responsive spermatozoa are the capacitated ones, it is reasonable that the role of this sperm responsiveness (comprising chemotaxis, enhancement of motility, and ultimately hyperactivation) might be to increase, over an extended period of time, the prospects that an egg will meet capacitated spermatozoa as soon as it ovulates, and that this is done by selecting capacitated spermatozoa and bringing them to the egg. This notion is well in line with a number of in vivo observations. (a) In hamsters, mice, rats, and rabbits, only capacitated or hyperactivated spermatozoa are transported from the oviductal isthmus to the ampulla (the site of fertilization). (b) The fertilizing potential of spermatozoa recovered from the oviduct (as expressed by the number of spermatozoa that should be supplied for fertilizing an egg, or by the time required for penetration of eggs in vitro) is much higher than that of ejaculated spermatozoa or spermatozoa recovered from the uterus. (c) In mammals, a considerable fraction of the spermatozoa ejaculated into the female reproductive tract is retained with reduced motility in storage sites; when ovulation occurs, some of them resume high motility and travel the distance between the storage and the fertilization sites within minutes (see Eisenbach and Ralt, 1992, for review).

TABLE 7

Distribution of physiological stages in the separated sperm subpopulations (revealed by staining with FITC-Con A)

| Population | Separation time (min) | Acrosome-intact | Capacitated | Acrosome-reacted | Non-stained |
|---|---|---|---|---|---|
| Enriched | 25 | 48% | 42% | 2% | 8% |
| Deficient | 25 | 57% | 29% | 10% | 4% |
| Enriched | 115 | 45% | 27% | 16% | 12% |
| Deficient | 115 | 45% | 45% | 6% | 4% |
| Original | (115) | 51% | 37% | 6% | 6% |

TABLE 8

The ratio of each physiological stage between the enriched and deficient subpopulations

| Separation time (min) | Acrosome-intact | Capacitated | Acrosome-reacted | Non-stained | No. of expts |
|---|---|---|---|---|---|
| 30 | 0.8 ± 0.1 | 2.2 ± 0.6 | 0.8 ± 0.5 | 1.2 ± 0.8 | 4 |
| 120 | 1.3 ± 0.6 | 0.5 ± 0.2 | 2.0 ± 1.0 | 2.0 ± 1.4 | 2 |

Example 6

Relative Chemotactic Activity of Different Fractions of Follicular Fluid obtained from a Size-Exclusion Column Follicular fluid was loaded on a size-exclusion HPLC column (TSK-125) (without undergoing first acetone precipitation as was in Example 3) and 8 fractions were eluted. The activity of the fractions ($10^4$-fold diluted) was analyzed by the capillary assay (6 experiments) and the 48-wells chemotaxis chamber (71 experiments) using 8 different donors. The results are shown in FIG. 22. Each column represents different number of experiments (indicated above the column), 6 repetitions in each experiment±S.E. The sperm concentration in the experiments was $2–20\times10^6$ cells/ml. The fractions of peak activity (at 16–18 min and 24–26 min) corresponded to the 13 kDa and <1.3 kDa chemotactic factors, respectively, indicating that the factors can be purified from follicular fluid even without the step of acetone precipitation.

REFERENCES

Biggers, J. D., W. K. Whitten and D. G. Whittingham. 1971. The culture of mouse embryos in vitro. In: Daniel J. D, (ed.), Methods in Mammalian Embryology. San Francisco: Freeman; pp. 86–116.

Burkman, L. J. 1990. Hyperactivated motility of human spermatozoa during in vitro capacitation and implications for fertility. In: Gagnon C, (ed.), Controls of Sperm Motility: Biological and Clinical Aspects. Boca Raton: CRC Press; pp. 303–329.

Dandekar, P. V. and M. M. Quigley. 1984. Laboratory setup for human in vitro fertilization. Fertil. Steril. 42: 1–11.

Eisenbach, M. and D. Ralt. 1992. Precontact mammalian sperm-egg communication and role in fertilization. Am. J. Physiol. 262 (Cell Physiol. 31) : C1095–C1101.

Florman, H. M. and D. F. Babcock. 1991. Progress toward understanding the molecular basis of capacitation. In: Elements of Mammalian Fertilization, P. M. Wassarman (ed.) CRC Press, Boca Raton, pp. 105–132.

Gnessi, L., M. R. Ruff, F. Fraioli and C. B. Pert. 1985. Demonstration of receptor-mediated chemotaxis by human spermatozoa. A novel quantitative bioassay. Exp. Cell Res. 161: 219–230.

Makler, A., A. Reichler, J. Stoller and P. D. Feigin. 1992. A new model for investigating in real time the existence of chemotaxis in human spermatozoa. Fertil. Steril. 57:1066–1074.

Ralt, D., M. Goldenberg, P. Fetterolf, D. Thompson, J. Dor, S. Mashiach, D. L. Garbers and M. Eisenbach. 1991. Sperm attraction of follicular factor(s) correlates with human egg fertilizability. Proc. Natl. Acad. Sci. USA 88:2840–2844.

Tesarik, J., Mendoza, C. and Carreras, A. 1993. Fast acrosome reaction measure - a highly sensitive method for evaluating Stimulus-Induced acrosome reaction. Fertil. Steril. 59: 424–430.

Yanagimachi, R. 1989. Sperm capacitation and gamete interaction. J. Report. Fert. Suppl. 38: 27–33.

I claim:

1. A purified chemotactic factor for human spermatozoa purifiable from human follicular fluid, said factor being of peptidic and of hydrophilic nature characterized by:
 (i) it is selected from a group consisting of a factor having a molecular size of about 13 kDa and a factor having an apparent molecular size smaller than 1.3 kDa, the molecular sizes being determined by high pressure gel filtration;
 (ii) it causes human sperm chemotaxis and chemokinesis and, ultimately, hyperactivation-like motility;
 (iii) its specific sperm chemotactic activity is concentration dependent;
 (iv) when purified from human follicular fluid or from a 90% acetone supernatant thereof by high pressure gel filtration as in (i) above, the 13 kDa chemotactic factor is eluted at 17.0–17.5 min and the <1.3 kDa chemotactic factor is eluted at 25.0–25.5 min, the specific sperm chemotactic activity (per protein content) of each factor being at least 1,000 fold higher than that of the follicular fluid from which said factor was Purified; and
 (v) when purified by reversed-phase HPLC from a supernatant of human follicular fluid precipitated with 90% acetone or from the active fractions eluted from the column described in (i) above, the sperm chemotactic activity of the 13 kDa factor is eluted at 20% acetonitrile, and the sperm chemotactic activity of the <1.3 kDa factor is eluted at 0% acetonitrile, the specific chemotactic activity (per protein content) of each factor being at least 10,000 fold higher than that of the follicular fluid from which said factor was purified.

2. A sperm chemotactic factor according to claim 1 having a molecular size of about 13±1 kDa.

3. A sperm chemotactic factor according to claim 1 having an apparent molecular size smaller than 1.3 kDa.

4. A method for the preparation of a sperm chemotactic factor according to claim 1 which comprises subjecting human follicular fluid to HPLC and recovering the fractions having sperm chemotactic activity.

5. A method according to claim 4 comprising first subjecting human follicular fluid to precipitation with a protein-precipitating organic solvent to obtain a precipitate and a supernatant, and then subjecting the supernatant to HPLC.

6. A method according to claim 4 wherein said HPLC is reversed-phase HPLC column.

7. A method according to claim 4, wherein the human follicular fluid is first applied to a size-exclusion HPLC column, thus obtaining two fractions showing sperm chemotactic activity one fraction containing the 13 kDa factor and the other fraction containing the <1.3 kDa factor, the two fractions are applied separately to a reversed-phase HPLC column, and the 13 kDa and <1.3 kDa factors are eluted at 20% and 0% acetonitrile, respectively.

8. A method according to claim 5 wherein the protein-precipitating organic solvent is 90% acetone.

9. Purified sperm chemotactic factor from human follicular fluid having a molecular size of about 13 kDa obtained by a method according to claim 4.

10. Purified sperm chemotactic factor from human follicular fluid having an apparent molecular size smaller than 1.3 kDa obtained by a method according to claim 4.

11. A pharmaceutical composition comprising a sperm chemotactic factor according to claim 1 and a pharmaceutically acceptable carrier.

12. A method for determining the fitness of human sperm for fertilization which comprises determining the ability of a sperm sample to be attracted to a sperm chemotactic factor in accordance with claim 1, whereby the greater the ability to be attracted to such factor, the greater the fitness of a population for fertilization.

13. In the process of fertilizing an ovum comprising causing a fertilizing sperm population to contact an ovum, the improvement wherein the fertilizing sperm population is pre-selected on the basis of its ability to be attracted to a sperm chemotactic factor in accordance with claim 1, those populations having the greatest degree of attraction to said factor being selected.

14. In the process of fertilizing an ovum in vitro comprising incubating a sperm population and ovum together in vitro, the improvement wherein the sperm and ovum are incubated in a solution to which is added a sperm chemotactic factor in accordance with claim 1.

15. In the process of fertilizing an ovum in vitro comprising incubating a sperm population and ovum together in vitro, the improvement wherein the sperm and ovum are incubated in a solution to which is added an amount effective for improving the probability of positive fertilization of a sperm chemotactic factor in accordance with claim 1.

16. A method according to claim 5 wherein said HPLC is reversed-phase HPLC.

17. A method according to claim 5, wherein said supernatant is first applied to a size-exclusion HPLC column, thus obtaining two fractions showing sperm chemotactic activity, one fraction containing the 13 kDa factor and the other fraction containing the <1.3 kDa factor, the two fractions are applied separately to a reversed-phase HPLC column, and the 13 kDa and <1.3 kDa factors are eluted at 20% and 0% acetonitrile, respectively.

18. Purified sperm chemotactic factor from human follicular fluid having a molecular size of about 13 kDa obtained by a method according to claim 7.

19. Purified sperm chemotactic factor from human follicular fluid having a molecular size of about 13 kDa obtained by a method according to claim 17.

20. Purified sperm chemotactic factor from human follicular fluid having an apparent molecular size smaller than 1.3 kDa obtained by a method according to claim 7.

21. Purified sperm chemotactic factor from human follicular fluid having an apparent molecular size smaller than 1.3 kDa obtained by a method according to claim 17.

* * * * *